US005945330A

United States Patent [19]
Hillman et al.

[11] Patent Number: 5,945,330
[45] Date of Patent: Aug. 31, 1999

[54] HUMAN LONGEVITY-ASSURANCE PROTEIN HOMOLOGS

[75] Inventors: Jennifer L. Hillman; Neil C. Corley, both of Mountain View; Purvi Shah; Preeti Lal, both of Sunnyvale, all of Calif.

[73] Assignee: Incyte Pharmaceuticals, Inc., Palo Alto, Calif.

[21] Appl. No.: 08/902,853

[22] Filed: Jul. 30, 1997

[51] Int. Cl.⁶ .......................... C07H 21/04; C12N 15/63; C12N 1/21
[52] U.S. Cl. .................. 435/252.3; 435/69.1; 435/320.1; 536/235
[58] Field of Search .......................... 536/23.5; 435/69.1, 435/320.1, 252.3

[56] References Cited

PUBLICATIONS

Hillier et al., "Homo sapiens cDNA clone 613400 5' similar to WP:CO9G4.1", XP002084175, E.M.B.L. Databases, Accession No: AA181797, Jan. 8, 1997.
Thompson, C.B., "Apoptosis in the Pathogenesis and Treatment of Disease", *Science,* 267: 1456–1462 (1995).
Jazwinski, S.M. et al., "A Single Gene Change Can Extend Yeast Life Span: The Role of RAS In Cellular Senescence", *Adv. Exp. Med. Biol.,* 330:45–53 (1993).
Chen, J.B. et al., "Prolongation of the yeast life span by the v–Ha–RAS oncogene", *Mol. Microbiol.,* 4: 2081–2086 (1990).
Sun, J. et al., "Divergent Roles of RAS1 and RAS2 in Yeast Longevity", *J. Biol. Chem.,* 269: 18638–18645 (1994).
D'mello, N.P. et al., "Cloning and Characterization of LAG1, a Longevity–assurance Gene in Yeast", *J. Biol. Chem.,* 269: 15451–15459 (1994) (GI 541568).
Jazwiniski, S.M., "Longevity, Genes, and Aging", *Science,* 273: 54–59 (1996).
Faragher, R.G.A. et al., "The gene responsible for Werner syndrome may be a cell division "counting" gene", *Proc. Natl. Acad. Sci. USA,* 90: 12030–12034 (1993).
Karlin, S. et al., "Multiple–alphabet amino acid sequence comparisons of the immunoglobulin k–chain constant domain", *Proc. Natl. Acad. Sci. USA,* 82: 8597–8601 (1985).
Wolozin, B. et al., "Participation of Presenilin 2 in Apoptosis: Enhanced Basal Activity Conferred by an Alzheimer Mutation", *Science,* 274: 1710–1713 (1996).
Wilson, R. et al., (Direct Submission), GenBank Sequence Database (Accession 1123105), National Center for Biotechnology Information, National Library of Medicine, Bethesda, Maryland, 20894 (GI 1123105) Dec. 1995.
Wilson, R. et al., (Direct Submission), GenBank Sequence Database (Accession U42438), National Center for Biotechnology Information, National Library of Medicine, Bethesda, Maryland, 20894 (GI 1123100; GI 1123105) Dec. 16, 1995).
Wilson, R. et al., "2.2 Mb of contiguous nucleotide sequence from chromosome III of C. elegans", *Nature,* 368: 32–38 (1994) GI 1123105).
Chanda, E.R. et al., (Direct Submission), GenBank Sequence Database (Accession 1675382), National Center for Biotechnology Information, National Library of Medicine, Bethesda, Maryland, 20894 (GI 1675382) Nov. 1996.
Chanda, E.R. et al., (Direct Submission), GenBank Sequence Database (Accession U76608), National Center for Biotechnology Information, National Library of Medicine, Bethesda, Maryland, 20894 (GI 1675381; GI 1675382) Nov. 1996.
D'mello, N.P. et al., (Direct Submission), GenBank Sequence Database (Accession 541568), National Center for Biotechnology Information, National Library of Medicine, Bethesda, Maryland, 20894 (GI 541568) Sep. 1994.
D'mello, N.P. et al., (Direct Submission), GenBank Sequence Database (Accession U08133), National Center for Biotechnology Information, National Library of Medicine, Bethesda, Maryland, 20894 (GI 541567; GI 541568).
New England Biolabs Catalog p. 91, 152–153 1993/1994.
Accession No. H19038 GenBank EST database Jun. 29, 1995.
Accession No. H38246 GenBank EST database Aug. 16, 1995.
Accession No. T68813 GenBank EST database Feb. 22, 1995.
Accession No. H38021 GenBank EST database Aug. 16, 1995.
Accession No. T68794 GenBank EST database Feb. 22, 1995.
Accession No. H19329 GenBank EST database Jun. 29, 1995.

*Primary Examiner*—Toni R. Scheiner
*Assistant Examiner*—Nancy A. Johnson
*Attorney, Agent, or Firm*—Sheela Mohan-Peterson; Lucy J. Billings; Incyte Pharmaceuticals Inc.

[57] ABSTRACT

The invention provides two human longevity-assurance protein homologs, designated individually as LAPH-1 and LAPH-2 and collectively as LAPH, and polynucleotides which identify and encode LAPH. The invention also provides expression vectors, host cells, agonists, antibodies and antagonists. The invention also provides methods for treating disorders associated with expression of LAPH.

8 Claims, 28 Drawing Sheets

```
5'  C TTT CCT TAC CTG TTT TTC CAG CTC ACC CAC TGC CAG CAG AGA ATG CTG TCC
                  9        18        27        36        45        54
      F   P   Y   L   F   F   Q   L   T   H   C   Q   Q   R   M   L   S

AGT TTC AAC GAG TGG TTT TGG CAG GAC AGG TTC TGG TTA CCA AAT GTC ACG
             63        72        81        90        99       108
      S   F   N   E   W   F   W   Q   D   R   F   W   L   P   N   V   T

TGG ACA GAG CTA GAA GAC CGG GAT GGC CGT GTC GTC TAC CCC CAC CAG GAC TTG
            117       126       135       144       153       162
      W   T   E   L   E   D   R   D   G   R   V   V   Y   P   H   Q   D   L

TTG GCA GCC CTG CCC CTG GCG CTG GTC CTC CTG ATG CGC CTT GCC TTT GAG
            171       180       189       198       207       216
      L   A   A   L   P   L   A   L   V   L   L   M   R   L   A   F   E

AGA ATT GGC CTG CCC CTG AGC CGG TGG CTG GGT GTG AGG GAT CAG ACC AGG
            225       234       243       252       261       270
      R   I   G   L   P   L   S   R   W   L   G   V   R   D   Q   T   R

AGG CAA GTG AAG CCC AAC GCC ACG CTG GAG AAA CAC TTC CTC ACG GAA GGG CAC
            279       288       297       306       315       324
      R   Q   V   K   P   N   A   T   L   E   K   H   F   L   T   E   G   H

AGG CCC AAG GAG CCC CAG CTG TCT CTC CTG GCC CAG TGT GGC CTC ACG CTG
            333       342       351       360       369       378
      R   P   K   E   P   Q   L   S   L   L   A   Q   C   G   L   T   L
```

FIG. 1A

```
CAG CAG ACC CAG CGA TGG TTC CGG AGA CGC CGG AAC CAG GAT CGA CCC CAG CTG
 Q   Q   T   Q   R   W   F   R   R   R   R   N   Q   D   R   P   Q   L

ACC AAG TTC TGT GAG GCC AGC TGG AGG TTT CTC TAC TTC TAC CTG TCC TCC TTC
 T   K   F   C   E   A   S   W   R   F   L   Y   F   Y   L   S   S   F

GTG GGC CTC TCG CTG TAC CTG GAG TCA CAC CTG TGG CTG GCA CCA GTA ATG
 V   G   L   S   L   Y   L   E   S   H   L   W   L   A   P   V   M

TGC TGG GAC AGG TAC CTC ACT CTG AAC CAG TCA CTG CTG AAG CCA TCC TAC TGG TGG TAC
 C   W   D   R   Y   L   T   L   N   Q   S   L   L   K   P   S   Y   W   W   Y

CTC TTG GAG CTG GGT TTC TAC AAG GAG CAG CTC TAC CTA ATC AGG CTG CCC TTT GAT GTC
 L   L   E   L   G   F   Y   K   E   Q   L   Y   L   I   R   L   P   F   D   V

AAG CGC AAG GAT TTC AAG GAG CAG GTG ATA CAC CAC TTC GTG GCG GTC ATC CTG
 K   R   K   D   F   K   E   Q   V   I   H   H   F   V   A   V   I   L

ATG ACC TTC TCC TAC AGT GCC AAC CTG CGC ATT GGC TCT CTG GTG CTG CTG
 M   T   F   S   Y   S   A   N   L   R   I   G   S   L   V   L   L
```

FIG. 1B

```
                      765            774            783            792            801            810
TTA CAC GAT TCC TCT GAC TAC CTG GAG GCC TGT AAG ATG GTC AAC TAC ATG
 L   H   D   S   S   D   Y   L   E   A   C   K   M   V   N   Y   M 819            828            837            846            855            864
CAG TAT CAG CAA GTG TGC GAC GCT CTC TTC CTC ATC TTC TCC TTT GTC TTC
 Q   Y   Q   Q   V   C   D   A   L   F   L   I   F   S   F   V   F 873            882            891            900            909            918
TAC ACC CGA CTG GTC CTC TTT CCC ACC CAG ATC CTC TAC ACC ACA TAC GAG
 Y   T   R   L   V   L   F   P   T   Q   I   L   Y   T   T   Y   E 927            936            945            954            963            972
TCC ATC AGC AAC AGG GGC CCC TTC TTC GGC TAC TAC TTC TTC AAC GGG CTT CTG
 S   I   S   N   R   G   P   F   F   G   Y   Y   F   F   N   G   L   L 981            990            999           1008           1017           1026
ATG TTG CAG CTG CAC GTG TTC TGG TCT TGC CTC ATT CTG CGC ATG CTC
 M   L   Q   L   H   V   F   W   S   C   L   I   L   R   M   L 1035           1044           1053           1062           1071           1080
TAT AGC TTC ATG AAG AAG GGC CAG ATG GAG AAG GAC ATT CGT AGT GAT GTA GAA
 Y   S   F   M   K   K   G   Q   M   E   K   D   I   R   S   D   V   E 1089           1098           1107           1116           1125           1134
GAA TCA GAC TCC AGT GAG GAG GCG GCG GCG CAG GAA CCT CTG CAG CTA AAG
 E   S   D   S   S   E   E   A   A   A   Q   E   P   L   Q   L   K
```

FIG. 1C

```
                                               1188
                            1179         CGG AGC CGG
        1170          GGC CCT            S   R
  1161       GCC CCC ACT GAT     P   R
1152   AGG CCA       A   P   T   D   G
  GGG CCC  R   P                              1242
1143  P                                   GGC GGG GCT
ACA GCT GGA                           CCG G   G   A
 T   A   G   G                   TAG P
AAC     T                    GCC A
N   G                    ACA T
                     ACA
               AAC AGG CAC
           ACC CAC
       CTG                           1296
   CGT                       TTC TGG GGT GAC TGG
GGG  L                       F   W   G   D   W
GCC R                   CTT
GTG A                TGC
V   G            CAG
              CCC
  1197    CCC
      TTG
  AAG                                         1350
1251                             CCG GGG TGG
GGC TGT                          P   G   W
                         GGG CAC
                     GGA
                 AGA
             TGG
         CCT
     GGG                                    1404
 CCT                             GCC CCC TTC
1305                             A   P   F
ACT GGC GCC               CCC CAC
                      CAG
                  CTC
              TGT
          ATC
      ATG
  AGG                                         1458
1359  CTG                        AGC TGG CTG
GTG                              S   W   L
              TCT
          CCT
      CAG
  TGG
TTT
1413
             GGA GCC                          1512
         ACA GAT CTG                  GGG GAG CCC CAG GCT GAA
     AAC TGG                          G   E   P   Q   A   E
 CTG
TTC CCT CTG                               1503
1467                              TGG GGG
                              TGG
                          CCT
                      TAG
                  CTG
              AGG
          TCC
      ACC
  GAC                     1494
GCC AGA            CTG TAG
                                                  1548
                                              AAA AGA A 3'
                        1539
                    AAT GGA GCC AAA
                ACA
            AAA
        ATT
    CCA
1521
AAG GGT
1530
```

FIG. 1D

```
                                         9                18               27              36               45              54
5'   A  GGG  AGG  AGA  GGC  GCG  GGG  AGC  CAG  GCC  TCG  GGG  CCT  CGG  AGC  AAC  CAC  CCG 63               72               81              90               99              108
     AGC  AGA  CGG  AGT  ACA  CGG  AGC  AGC  GGC  CCC  GCC  AAC  GCT  GCC  GCC  GGG 117              126              135             144              153             162
     ATG  CTC  CAG  ACC  TTG  TAT  GAT  TAC  TTC  TGG  GAA  CGT  CTG  TGG  CTG  CCT  GTG
      M    L    Q    T    L    Y    D    Y    F    W    E    R    L    W    L    P    V 171              180              189             198              207             216
     AAC  TTG  ACC  TGG  GCC  GAT  CTA  GAA  GAC  CGA  GAT  GGA  CGT  GTC  TAC  GCC  AAA  GCC
      N    L    T    W    A    D    L    E    D    R    D    G    R    V    Y    A    K    A 225              234              243             252              261             270
     TCA  GAT  CTC  TAT  ATC  ACG  CTG  CCC  GCC  TTG  CTG  TTC  CTC  ATC  GTT  CGA  TAC
      S    D    L    Y    I    T    L    P    A    L    L    F    L    I    V    R    Y 279              288              297             306              315             324
     TTC  TTT  GAG  CTG  TAC  GTG  GCT  ACA  CCA  CTG  CCC  GCT  CTT  TTG  AAC  ATA  AAG  GAG
      F    F    E    L    Y    V    A    T    P    L    A    L    L    N    I    K    E 333              342              351             360              369             378
     AAA  ACT  CGG  CTG  CGG  GCA  CCT  CCC  AAC  GCC  ACC  TTG  GAA  CAT  TTC  TAC  CTG  ACC
      K    T    R    L    R    A    P    P    N    A    T    L    E    H    F    Y    L    T
```

FIG. 2A

```
387                 396                 405                 414                 423                 432
AGT GGC AAG         CAG CCC AAG         CAG GTG GAA         GTA GAG CTT         TTG TCC CGG         CAG AGC GGG
 S   G   K           Q   P   K           Q   V   E           V   E   L           L   S   R           Q   S   G 441                 450                 459                 468                 477                 486
CTC TCT GGC         CGC CAG AAG         TTC CGA GAG         CGT TTC CGT         CGC CGC AAC         CAG GAC CGG
 L   S   G           R   Q   K           F   R   E           R   F   R           R   R   N           Q   D   R 495                 504                 513                 522                 531                 540
CCC AGT CTC         CTC AAG TTC         CGA GAA GCC         AGC GAA TGG         AGA TTC ACA         TTT TAC CTG
 P   S   L           L   K   F           R   E   A           S   E   W           R   F   T           F   Y   L 549                 558                 567                 576                 585                 594
ATT GCC TTC         ATT GCC GGC         ATG GCC ATT         GTC GAT AAA         CCC TGG TTC         TAT GAC
 I   A   F           I   A   G           M   A   I           V   D   K           P   W   F           Y   D 603                 612                 621                 630                 639                 648
AAA GTT TGG         GAG GGA TAT         GGC GTC ATT         CCC ATA CAG         TGG CCT TCC         CAG TAT
 K   V   W           E   G   Y           G   V   I           P   I   Q           W   P   S           Q   Y 657                 666                 675                 684                 693                 702
TAC TAC ATG         ATT GAA CTT         TCC TTC TAC         TGG AGC ACT         ATC CCT TCC         ATT GCC
 Y   Y   M           I   E   L           S   F   Y           W   S   T           I   P   S           I   A 711                 720                 729                 738                 747                 756
TCT GAT GTC         AAG CGA AAG         GAT TTC AAG         GAA CAG ATC         ATC CAC CAT         GTG GCC ACC
 S   D   V           K   R   K           D   F   K           E   Q   I           I   H   H           V   A   T
```

FIG. 2B

```
     765      774      783      792      801      810
ATC ATT CTC ATC AGC TTT TCC TGG AAT TAC ATC CGA GCT GGG ACT CTA
 I   I   L   I   S   F   S   W   N   Y   I   R   A   G   T   L 819      828      837      846      855      864
ATG GCT CTG CAT GAC TCT TCC GAT TAC CTG GAG TCA GCC AAG ATG TTT
 M   A   L   H   D   S   S   D   Y   L   E   S   A   K   M   F 873      882      891      900      909      918
AAC TAC GCG GGA AAG AAC ACC TGC AAC AAC ATC TTC GTC TTC GCC ATT
 N   Y   A   G   K   N   T   C   N   N   I   F   V   F   A   I 927      936      945      954      963      972
GTT TTT ATC ATC ACC CGA CTG GTC ATC CTG CCC TTC TGG ATC CTG CAT TGC ACC
 V   F   I   I   T   R   L   V   I   L   P   F   W   I   L   H   C   T 981      990      999      1008     1017     1026
CTG GTG TAC CCA CTG GAG CTC TAT CCT GCC TTC TTT GGC TAT TAC TTC TTC AAT
 L   V   Y   P   L   E   L   Y   P   A   F   F   G   Y   Y   F   F   N 1035     1044     1053     1062     1071     1080
TCC ATG ATG GGA GTT CTA CAG CTG CTG CAT ATC TTC TGG GCC TAC CTC ATT TTG
 S   M   M   G   V   L   Q   L   L   H   I   F   W   A   Y   L   I   L 1089     1098     1107     1116     1125     1134
CGC ATG GCC CAC AAG TTC ATA ACT GGA AAG CTG GTA GAA GAT GAA CGC AGT GAC
 R   M   A   H   K   F   I   T   G   K   L   V   E   D   E   R   S   D
```

```
     1143        1152        1161        1170        1179        1188
CGG GAA ACA GAG AGC TCA GAG GGG GAG GCT GCA GCT GGG GGA GGA GCA
 R   E   T   E   S   S   E   G   E   A   A   A   G   G   G   A 1197        1206        1215        1224        1233        1242
AAG AGC CGG CCC CTA GCC AAT GGC CAC CCC ATC CTC AAT AAC CAT CGT AAG
 K   S   R   P   L   A   N   G   H   P   I   L   N   N   H   R   K 1251        1260        1269        1278        1287        1296
AAT GAC TGA ACC ATT ATT CCA GCT GCC TCC CAG ATT AAT GCA TAA AGC CAA GGA
 N   D 1305        1314        1323        1332        1341        1350
ACT ACC CCG CTC CTA TAG GCG CTA TAG GGT CAC TTT AAG CTC TGG GGA AAA AGG AGA 1359        1368        1377        1386        1395        1404
AAG TGA GAG GAG AGT TCT CTG CAT CCT CCC TCC TTG CTT GTC ACC CAG TTG CCT 1413        1422        1431        1440        1449        1458
TTA AAC CAA ATT CTA ACC AGC CTA TCC CCA GGT AGG GGG ACG TTG GTT ATA TTC 1467        1476        1485        1494        1503        1512
TGT TAG AGG GGG ACG GTC GTA TTT TCC TCC CTA CCC GCC AAG TCA TCC TTT CTA 1521        1530        1539        1548        1557        1566
CTG CTT TTG AGG CCC TCC CTC AGC TCT CTG TGG GTA GGG GTT ACA ATT CAC ATT
```

```
      1575            1584            1593           1602           1611           1620
CCT TAT TCT GAG AAT TTG GCC CCA GCT GTT TGC CTT TGA CTC CCT GAC CTC CAG
      1629            1638            1647           1656           1665           1674
AGC CAG GGT TGT GCC TTA TTG TCC CAT CTG TGG GCC TCA TTC TGC CAA AGC TGG
      1683            1692            1701           1710           1719           1728
ACC AAG GCT AAC CTT TCT AAG CTC CCT AAC TTG GGC CAG AAA CCA AAG CTG AGC
      1737            1746            1755           1764           1773           1782
TTT TAA CTT TCT CCC TCT ATG ACA CAA ATG AAT TGA GGG TAG GAG GAG GGT GCA
      1791            1800            1809           1818           1827           1836
CAT AAC CCT TAC CCT ACC TCT GCC AAA AAG TGG GGG CTG TAC TGG GGA CTG CTC
      1845            1854            1863           1872           1881           1890
GGA TGA TCT TTC TTA GTG CTA CTT CTT TCA GCT GTC CCT GTA GCG ACA GGT CTA
      1899            1908            1917           1926           1935           1944
AGA TCT GAC TGC CTC CTC CTT TCT CTG GCC TCT TCC CCC TTC CCT CTT CTC TTC
      1953            1962            1971           1980           1989           1998
AGC TAG GCT AGC TGG TTT GGA GTA GAA CTA ATT CTA ATT TTT ATT TAT
      2007            2016            2025           2034           2043           2052
TAA ATA TTT GGG GTT TTG GTT TTA AAG CCA GAA TTA CGG CTA GCA CCT AGC ATT
```

FIG. 2E

```
      2061          2070          2079     2088          2097      2106
TCA GCA GAG GGA CCA TTT TAG ACC AAA ATG TAC TGT TAA TGG GTT TTT TTT TAA
      2115          2124          2133     2142          2151      2160
AAT TAA AAG ATT AAA TAA AAA ATA TTA AAA AAA AAA AAA AAG GGG GGG
GG 3'
```

HUMAN LONGEVITY-ASSURANCE PROTEIN HOMOLOGS

FIELD OF THE INVENTION

This invention relates to nucleic acid and amino acid sequences of two human longevity-assurance protein homologs and to the use of these sequences in the diagnosis, prevention, and treatment of disorders associated with aberrant regulation of cellular homeostasis and disorders associated with aging.

BACKGROUND OF THE INVENTION

Normal growth, differentiation, and survival in multicellular organisms requires a carefully regulated balance, or homeostasis, between the production and destruction of cells in tissues throughout the body. Cell division is a carefully coordinated process with numerous checkpoints and control mechanisms. These mechanisms are designed to regulate DNA replication and to prevent inappropriate or excessive proliferation. In contrast, apoptosis is a genetically controlled process by which unneeded or damaged cells are eliminated without causing the tissue destruction and inflammatory responses that are often associated with acute injury and necrosis.

A variety of ligands and their cellular receptors, enzymes, tumor suppressors, viral gene products, pharmacological agents, and inorganic ions have important positive or negative roles in regulating and implementing the apoptotic destruction of a cell. Although some specific components of the apoptotic pathway have been identified and characterized, many interactions between the proteins involved are undefined, leaving major aspects of the pathway unknown (Thompson, C. B. (1995) Science 267:1456–1462).

Mammalian cells in culture can be grown for only a limited number of cell divisions after which they cease proliferation and exhibit the morphological changes associated with cellular senescence. Evidence in support of a genetic determinant for aging has been obtained in various organisms. For instance, in the yeast *Saccharomyces cerevisiae*, the patterns of expression of certain genes change in a specific manner during the life span, and these changed patterns suggest that the aging process is subject to gene regulation.

Controlled expression of the transforming gene of Harvey murine sarcoma virus (v-Ha-ras) was found to extend yeast life span (as measured by the number of cell divisions) nearly two-fold (Jazwinski, S. M. et al. (1993) Adv. Exp. Med. Biol. 330: 45–53; Chen, J. B. et al. (1990) Mol. Microbiol. 4: 2081–2086). RAS1 and RAS2, which are yeast homologs of the v-Ha-ras oncogene, play central roles in the integration of cell growth and the cell cycle in yeast. The primary role of these RAS proteins in yeast is the GTP-dependent regulation of adenylate cyclase activity. Curiously, mutations in RAS1 and RAS2 have opposite effects on yeast life span. Sun, J. et al. (1994; J. Biol. Chem 269:18638–18645) observed that deletion of RAS1 lengthened life span while deletion of RAS2 decreased life span. Elevated expression of yeast RAS2 led to a 30% increase in life span and postponed the senescence-related increase in cell generation time seen during yeast aging. No life span extension was observed by overexpression of RAS1, although both RAS1 and RAS2 mRNA and protein levels declined with replicative age.

D'mello, N. P. et al. (1994; J. Biol. Chem. 269:15451–15459) isolated a yeast gene denoted longevity-assurance gene-1 (LAG1). LAG1 expression is highest in young cells and decreases as yeast cells age. The predicted translation product is a 411 amino acid protein (denoted LAG1p or LAP1) which contains clusters of potential phosphorylation sites near the N- and C-termini and multiple potential transmembrane domains. Deletion of LAG1 resulted in a significant increase in the mean and maximum number of cell divisions; the mean life span increased from 17 to 25 cell divisions, and the maximum life span increased from 25 to 37 cell divisions. D'mello et al. (supra) proposed that the expression of LAG1 in young yeast cells may set a threshold which determines the extent to which the cells can divide. Deletion of LAG1 apparently alters this threshold, and a different gene(s) may then become the limiting factor in longevity (D'mello et al., supra). LAC1, described as a virtual copy of LAG1, is found on a different yeast chromosome and also alters longevity (Jazwinski, S. M. (1996) Science 273:54–59; Kirchman, P. A. and Jazwinski, S. M., unpublished).

Aberrant regulation of cellular homeostasis is a significant factor in the pathogenesis of human disease. For example, inappropriate cell survival can cause or contribute to diseases such as cancer, autoimmune diseases, and inflammation. In contrast, increased apoptosis can cause or contribute to immunodeficiency diseases such as AIDS, neurodegenerative disorders including Alzheimer's disease, and myelodysplastic syndromes (Thompson, C. B. (1995) Science 267:1456–1462).

Furthermore, numerous diseases and disorders are associated with aging. Diseases which show age-dependent onset of symptoms include Alzheimer's disease, Pick's disease, Huntington's disease, Parkinson's disease, adult onset myotonic dystrophy, multiple sclerosis, adult onset leukodystrophy, diabetes mellitus, arteriosclerosis, and cancer.

Patients who suffer from premature aging syndromes exhibit numerous defects associated with more advanced age groups. Symptoms of Werner's syndrome include scleroderma-like skin changes, cataract, subcutaneous calcification, premature arteriosclerosis, and diabetes mellitus. A striking aspect of Werner's syndrome, presumably arising from the same genetic defect, is a dramatic shortening of the replicative life-span of dermal fibroblasts in vitro (Faragher, R. G. et al. (1993) Proc. Natl. Acad. Sci. USA 90:12030–12034). Fibroblasts from Werner's syndrome patients exit irreversibly from the cell cycle at a faster rate than do normal cells, although they generally start off with a good replicative ability. Faragher, R. G. et al (supra) proposed that the Werner syndrome gene is a "counting" gene which controls the number of times that human cells are able to divide before terminal differentiation.

The discovery of two new human longevity-assurance protein homologs and the polynucleotides encoding them satisfies a need in the art by providing new compositions which are useful in the diagnosis, prevention and treatment of disorders associated with aberrant regulation of cellular homeostasis and disorders associated with aging.

SUMMARY OF THE INVENTION

The invention features two substantially purified polypeptides, human longevity-assurance protein homologs (designated collectively as LAPH and individually as LAPH-1 and LAPH-2) having the amino acid sequences shown in SEQ ID NO:1 and SEQ ID NO:3, respectively, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding LAPH-1 under conditions suitable for the expression of the polypeptide; and b) recovering the polypeptide from the host cell culture.

The invention also provides a pharmaceutical composition comprising a substantially purified LAPH-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising at least a fragment of the amino acid sequence of SEQ ID NO:1.

Still further, the invention provides a purified agonist of the polypeptide of SEQ ID NO:1.

The invention also provides a method for treating or preventing a disorder associated with aberrant regulation of cellular homeostasis comprising administering to a subject in need of such treatment an effective amount of an antagonist to LAPH-1.

The invention also provides a method for treating or preventing a disorder associated with aging comprising administering to a subject in need of such treatment an effective amount of an antagonist to LAPH-1.

The invention also provides a method for detecting a polynucleotide which encodes LAPH-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding LAPH-1 in the biological sample. In one aspect the nucleic acid material of the biological sample is amplified by the polymerase chain reaction prior to hybridization.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4 or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding LAPH-2 under conditions suitable for the expression of the polypeptide; and b) recovering the polypeptide from the host cell culture.

The invention also provides a pharmaceutical composition comprising a substantially purified LAPH-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for treating or preventing a disorder associated with aberrant regulation of cellular homeostasis comprising administering to a subject in need of such treatment an effective amount of an antagonist to LAPH-2.

The invention also provides a method for treating or preventing a disorder associated with aging comprising administering to a subject in need of such treatment an effective amount of an antagonist to LAPH-2.

The invention also provides a method for detecting a polynucleotide which encodes LAPH-2 in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding LAPH-2 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of LAPH-1. The alignment was produced using MACDNA- SIS PRO™ software (Hitachi Software Engineering Co. Ltd. San Bruno, Calif.).

FIGS. 2A, 2B, 2C, 2D, 2E and 2F show the amino acid sequence (SEQ ID NO:3) and nucleic acid sequence (SEQ ID NO:4) of LAPH-2.

Figure 3A:
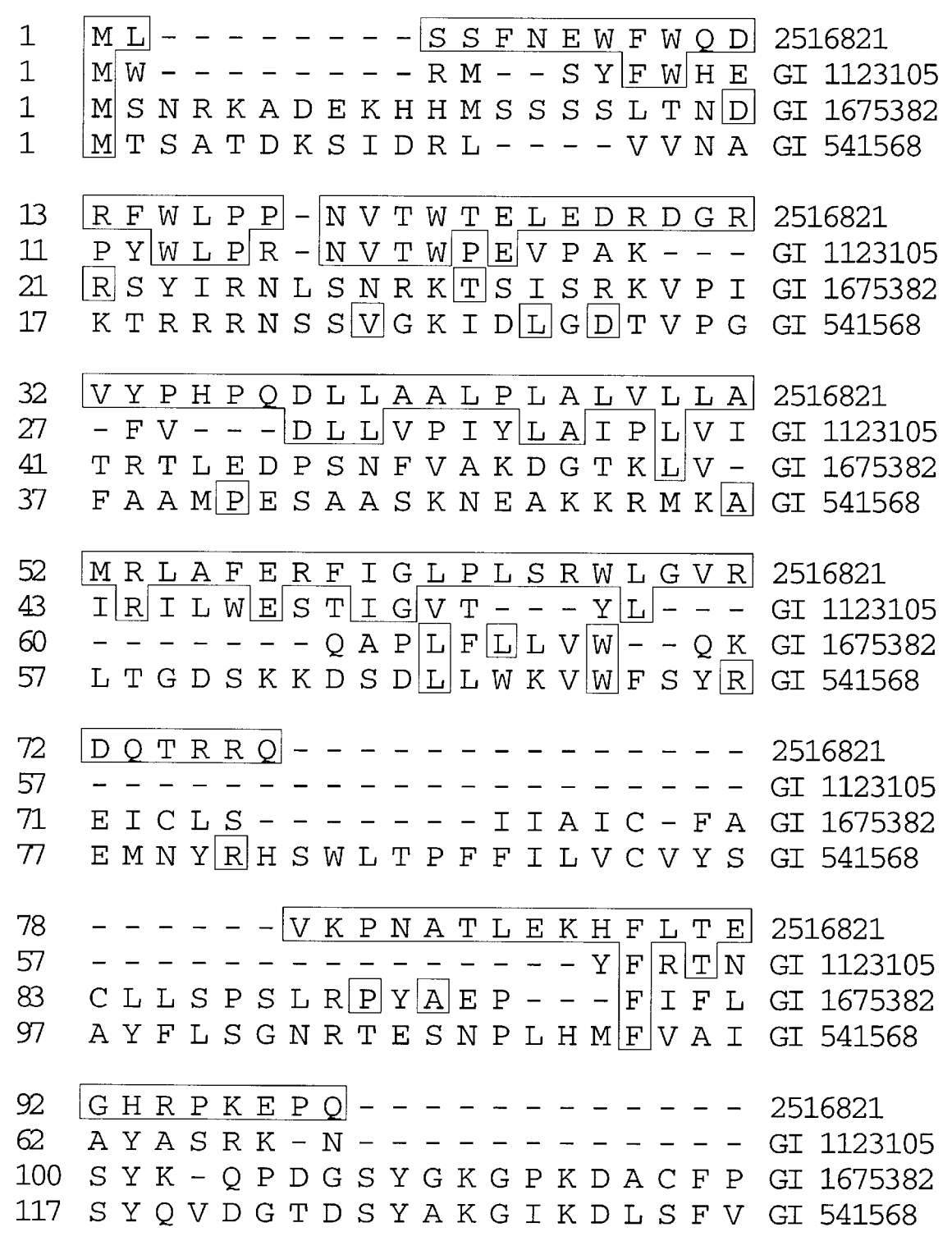
Figure 3B:
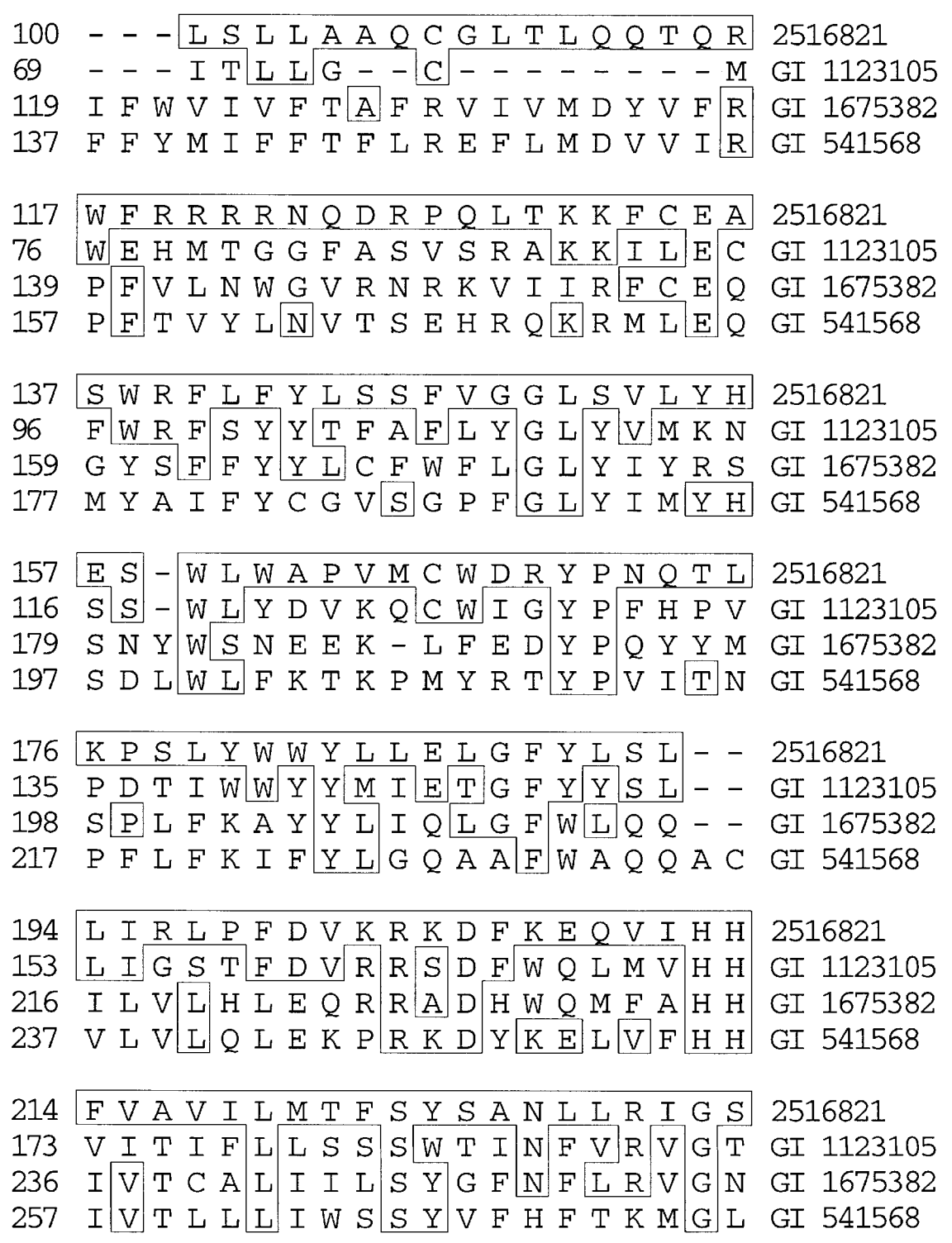
Figure 3C:
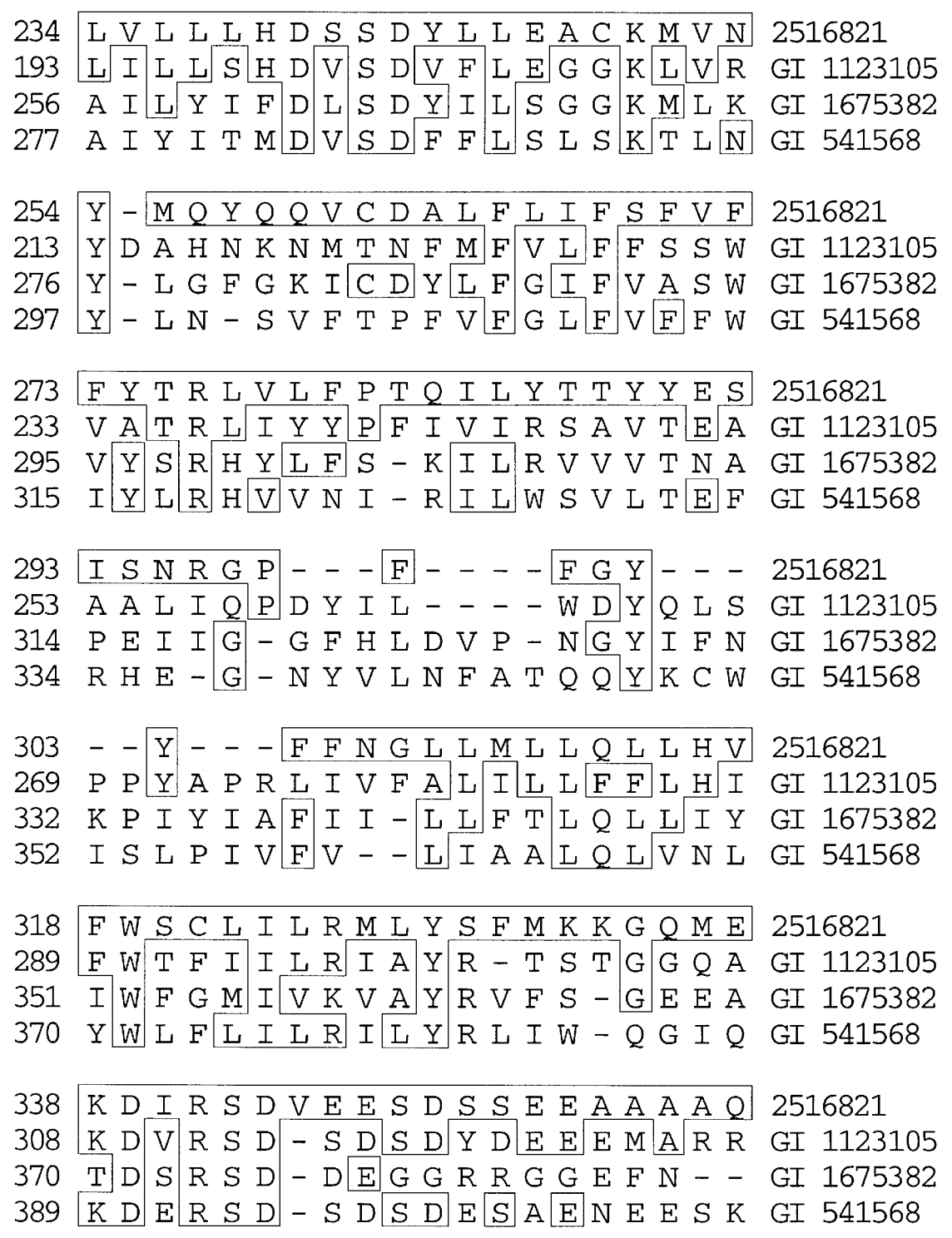
Figure 3D:
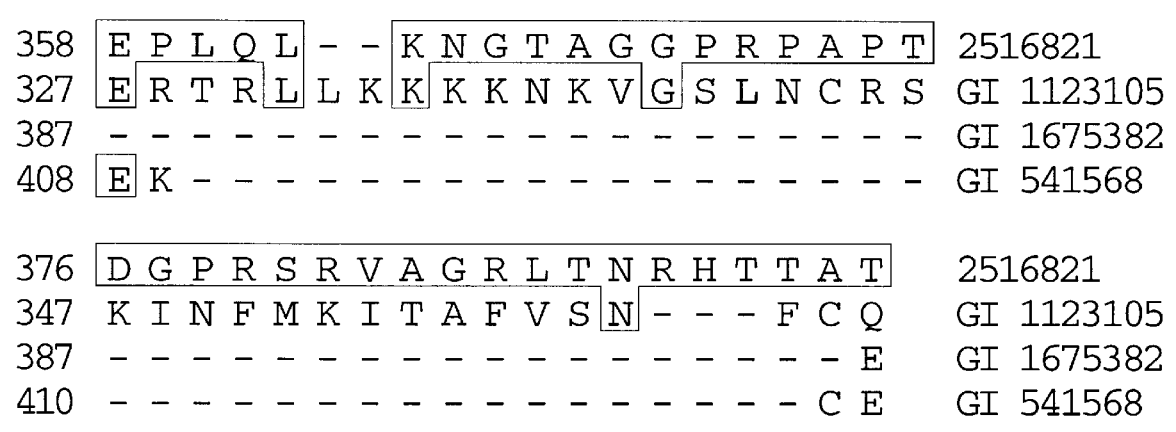

FIGS. 3A, 3B, 3C, and 3D show the amino acid sequence identity alignments among LAPH-1 (2516821; SEQ ID NO:1), Caenorhabditis elegans LAP-1 homolog (GI 1123105; SEQ ID NO:5), longevity assurance factor (LAF) from Schizosaccharomyces pombe (GI 1675382; SEQ ID NO:6), and LAP-1 from Saccharomyces cerevisiae (GI 541568; SEQ ID NO:7); aligned amino acids with identical functional groups are boxed. The alignment was produced using the multisequence alignment program of DNASTAR software (DNASTAR Inc, Madison Wis.).

Figure 4A:
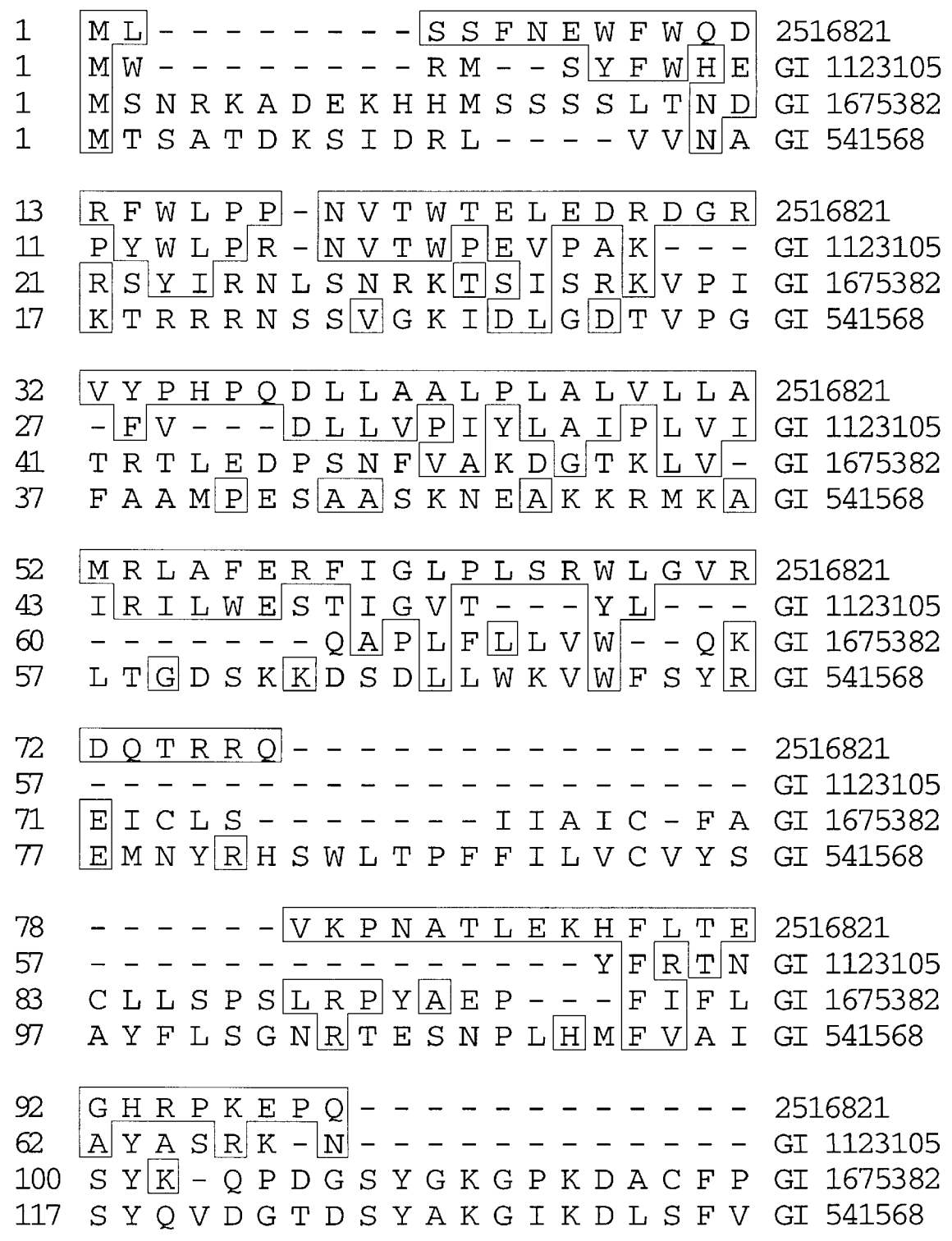
Figure 4B:
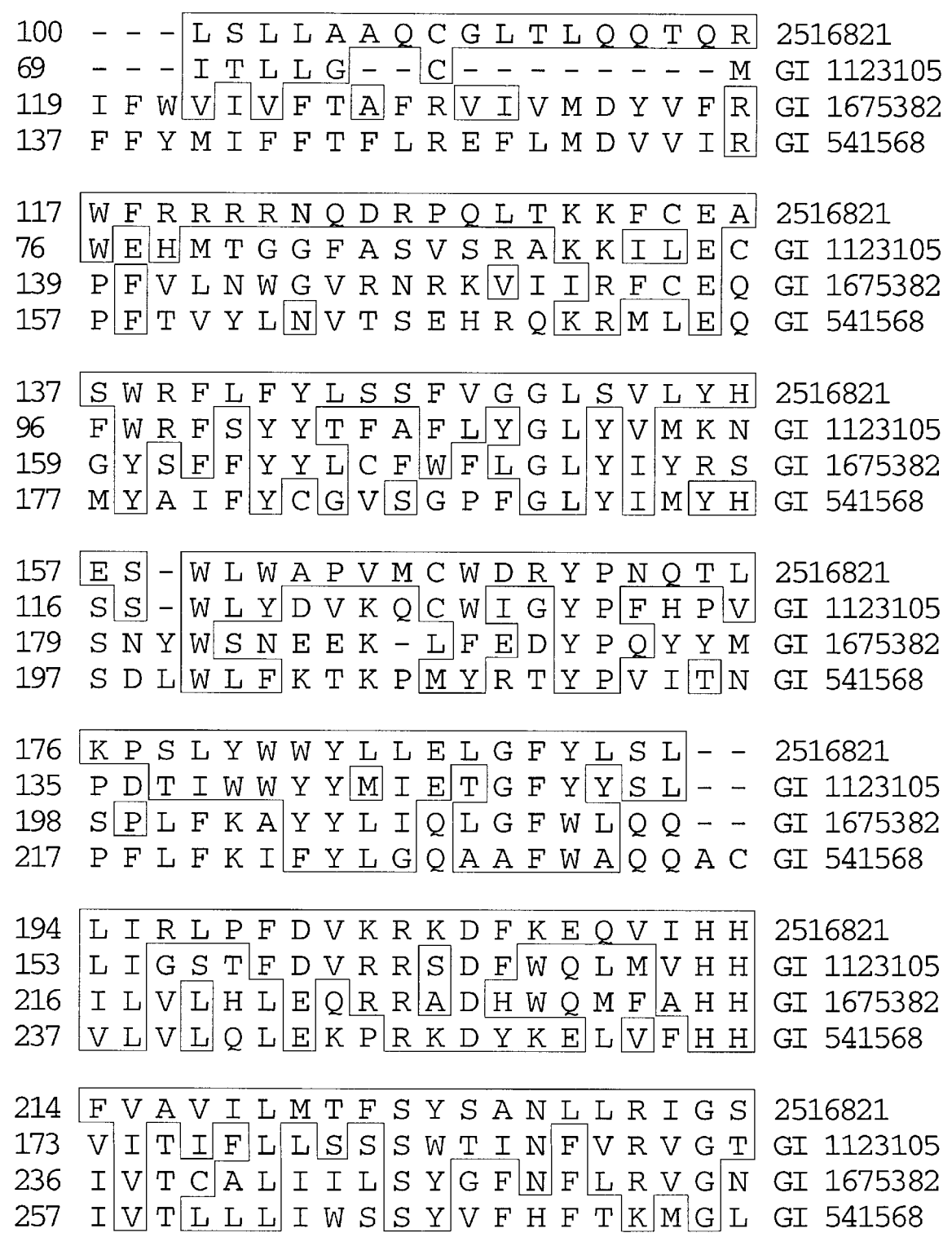
Figure 4C:
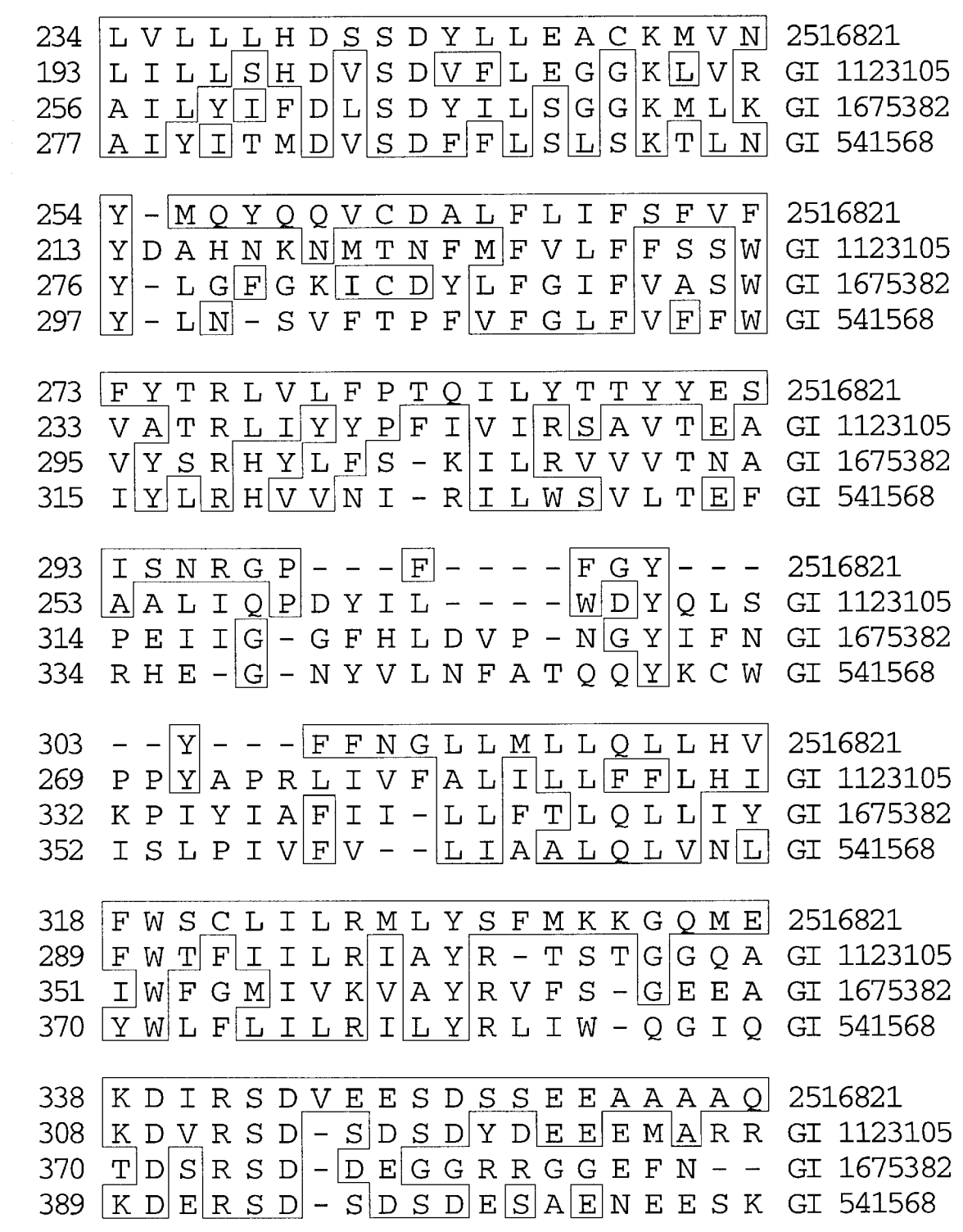
Figure 4D:
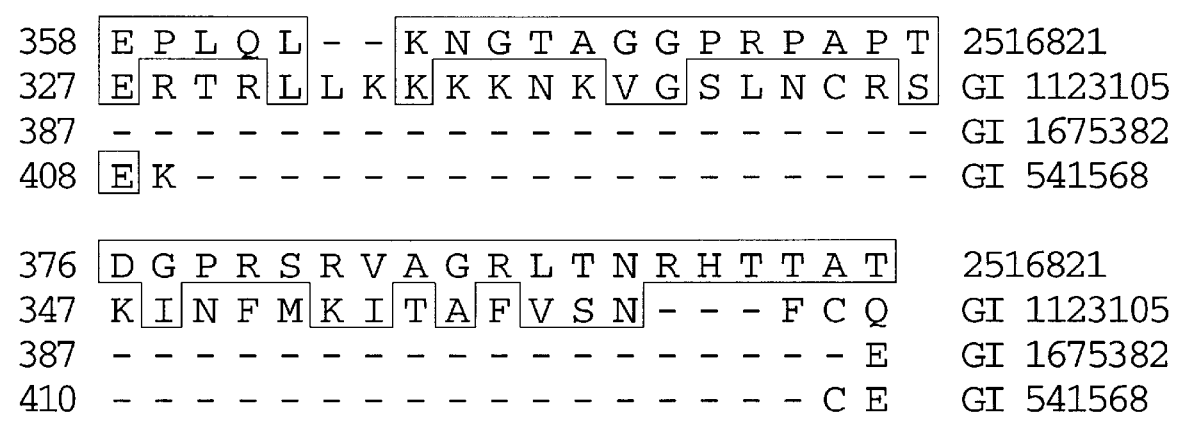

FIGS. 4A, 4B, 4C, and 4D show the amino acid sequence similarity alignments among LAPH-1 (2516821; SEQ ID NO:1), C. elegans LAP-1 homolog (GI 1123105; SEQ ID NO:5), longevity assurance factor (LAF) from S. pombe (GI 1675382; SEQ ID NO:6), and LAP-1 from S. cerevisiae (GI 541568; SEQ ID NO:7); aligned amino acids with chemically similar functional groups are boxed.

Figure 5A:
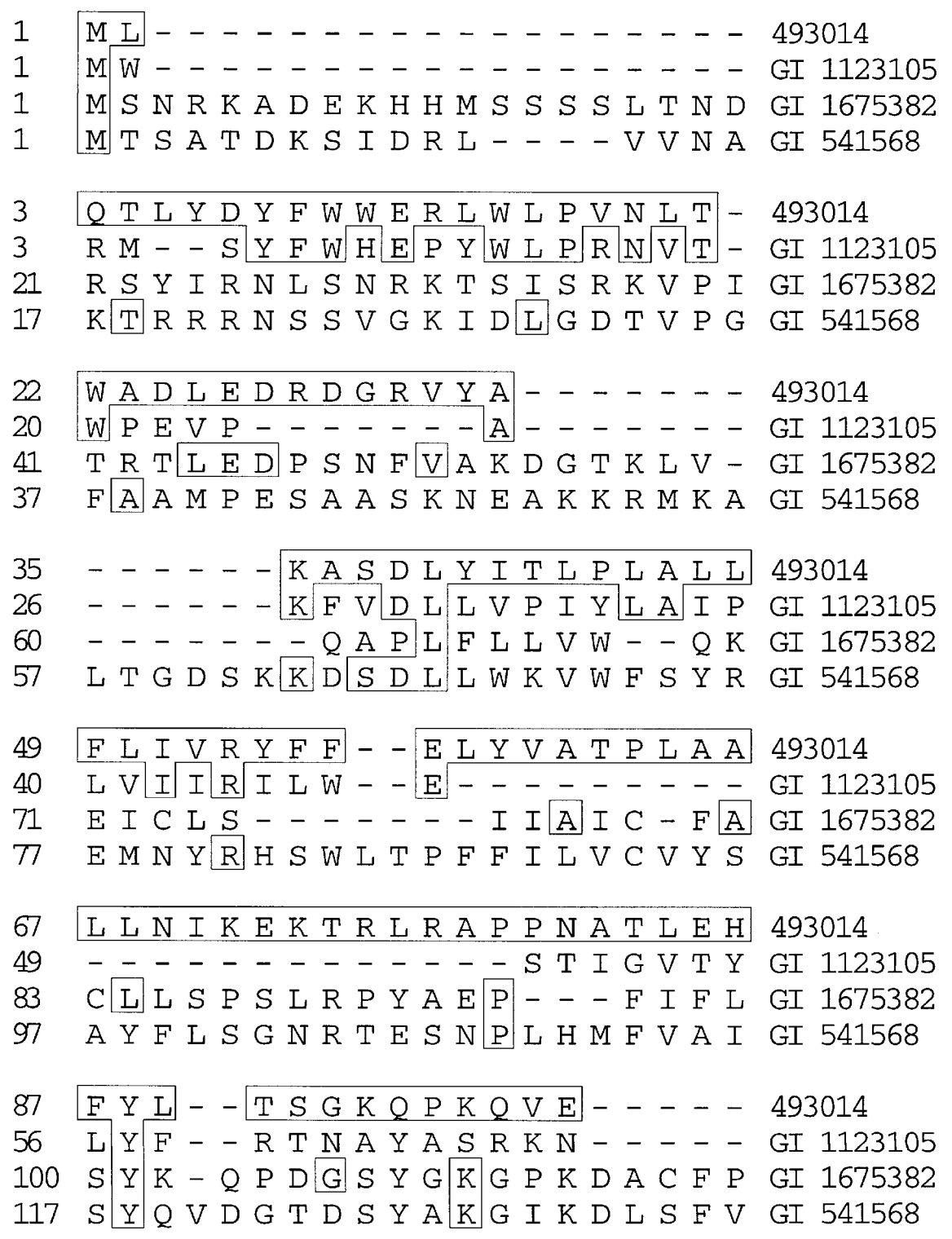
Figure 5B:
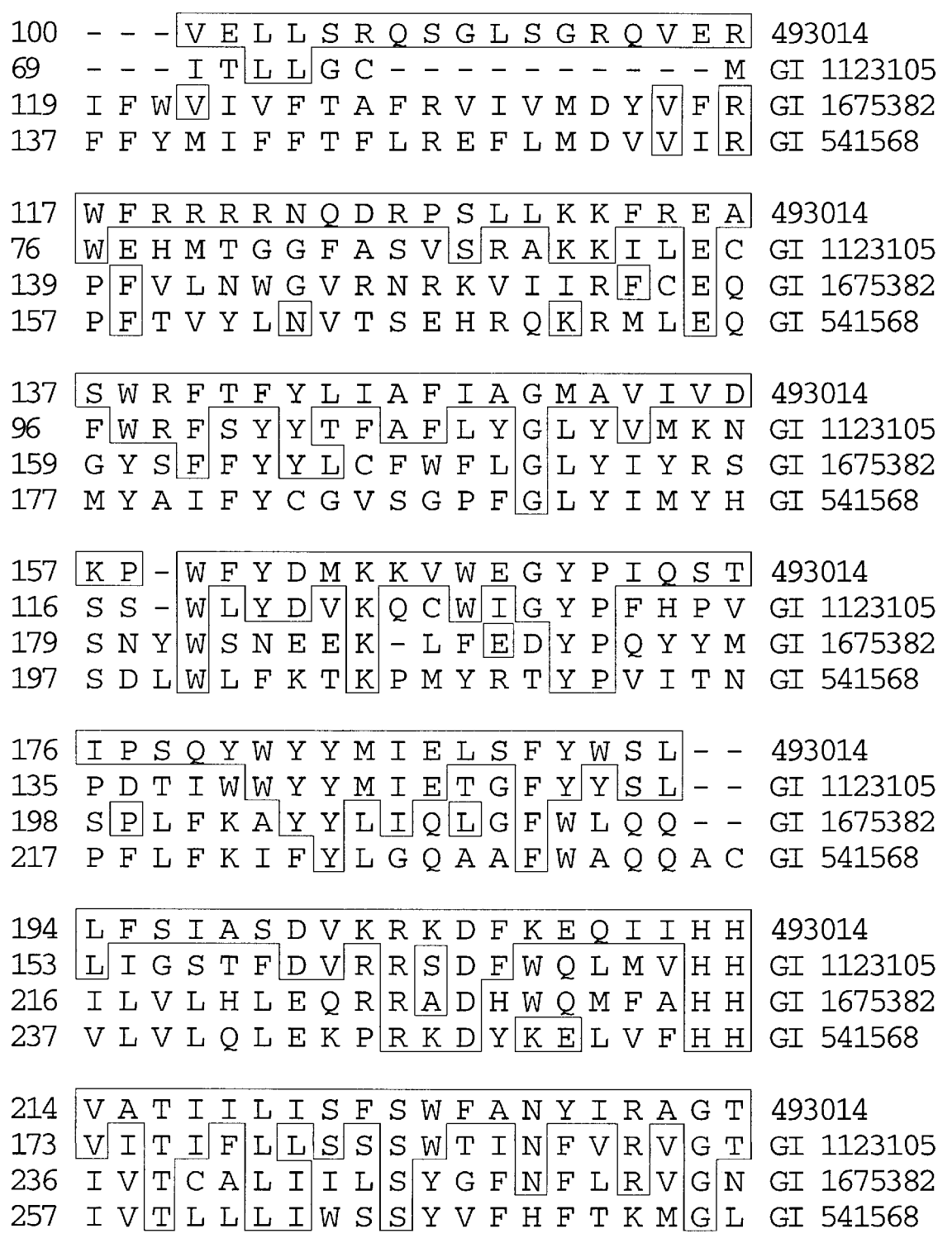
Figure 5C:
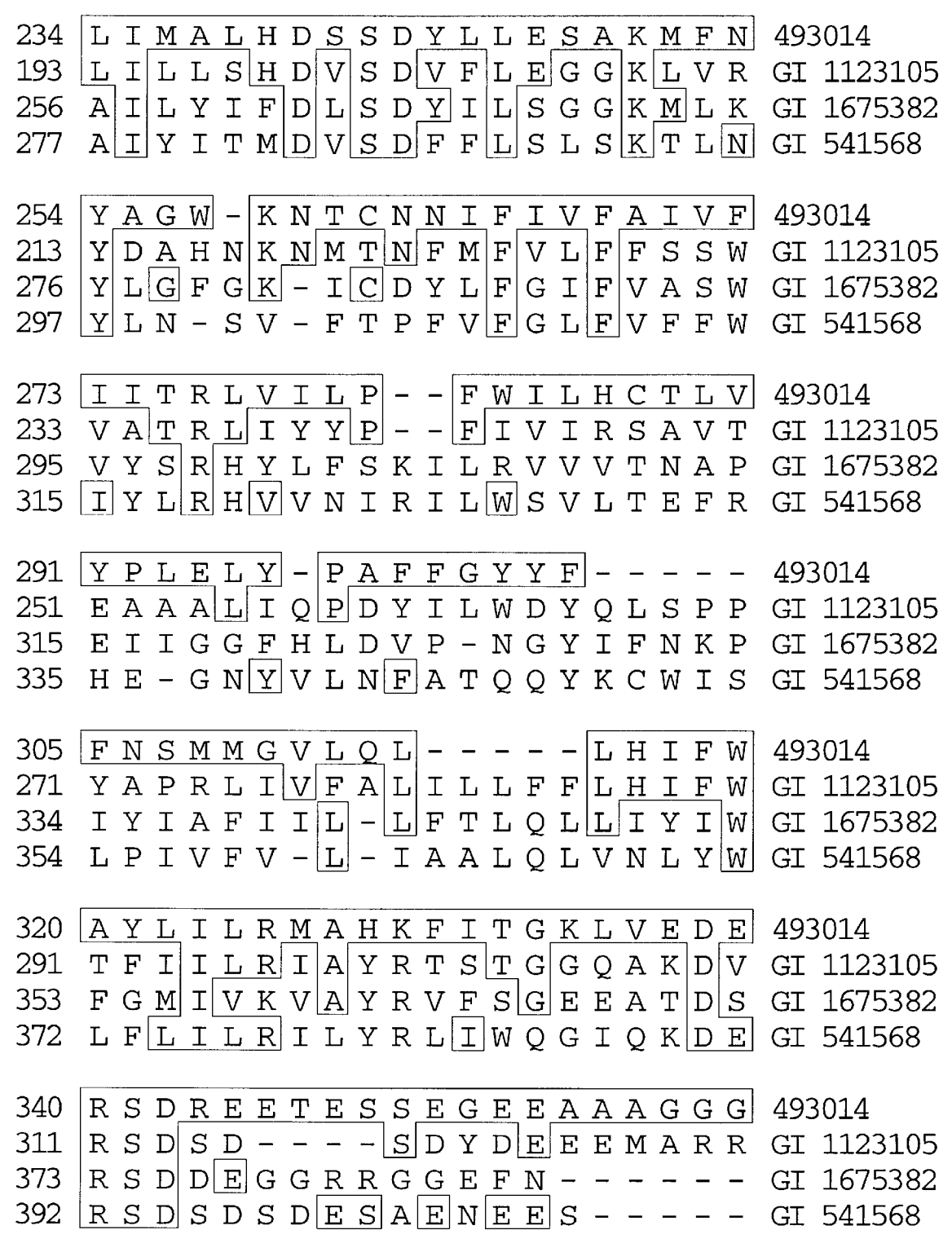
Figure 5D:
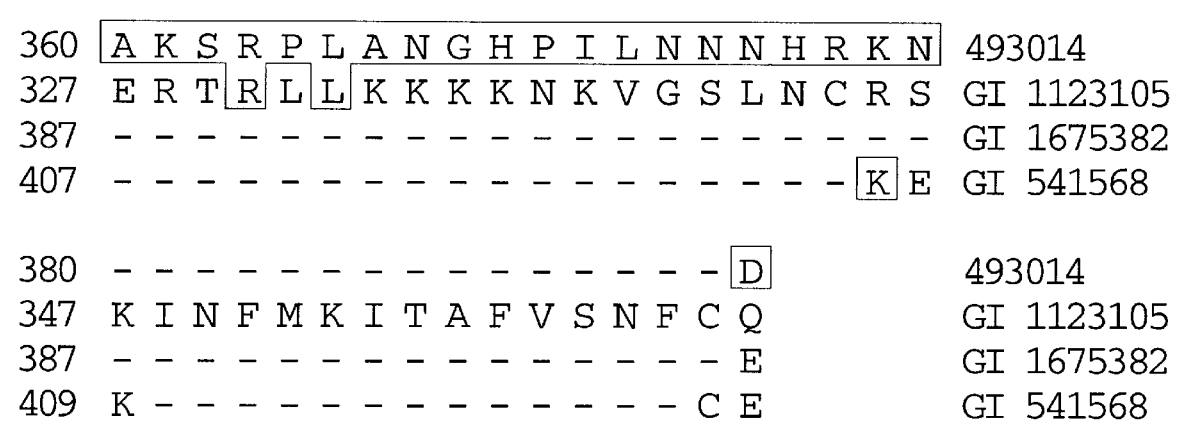

FIGS. 5A, 5B, 5C, and 5D show the amino acid sequence identity alignments among LAPH-2 (493014; SEQ ID NO:3), C. elegans LAP-1 homolog (GI 1123105; SEQ ID NO:5), longevity assurance factor (LAF) from S. pombe (GI 1675382; SEQ ID NO:6), and LAP-1 from S. cerevisiae (GI 541568; SEQ ID NO:7); aligned amino acids with identical functional groups are boxed.

Figure 6A:
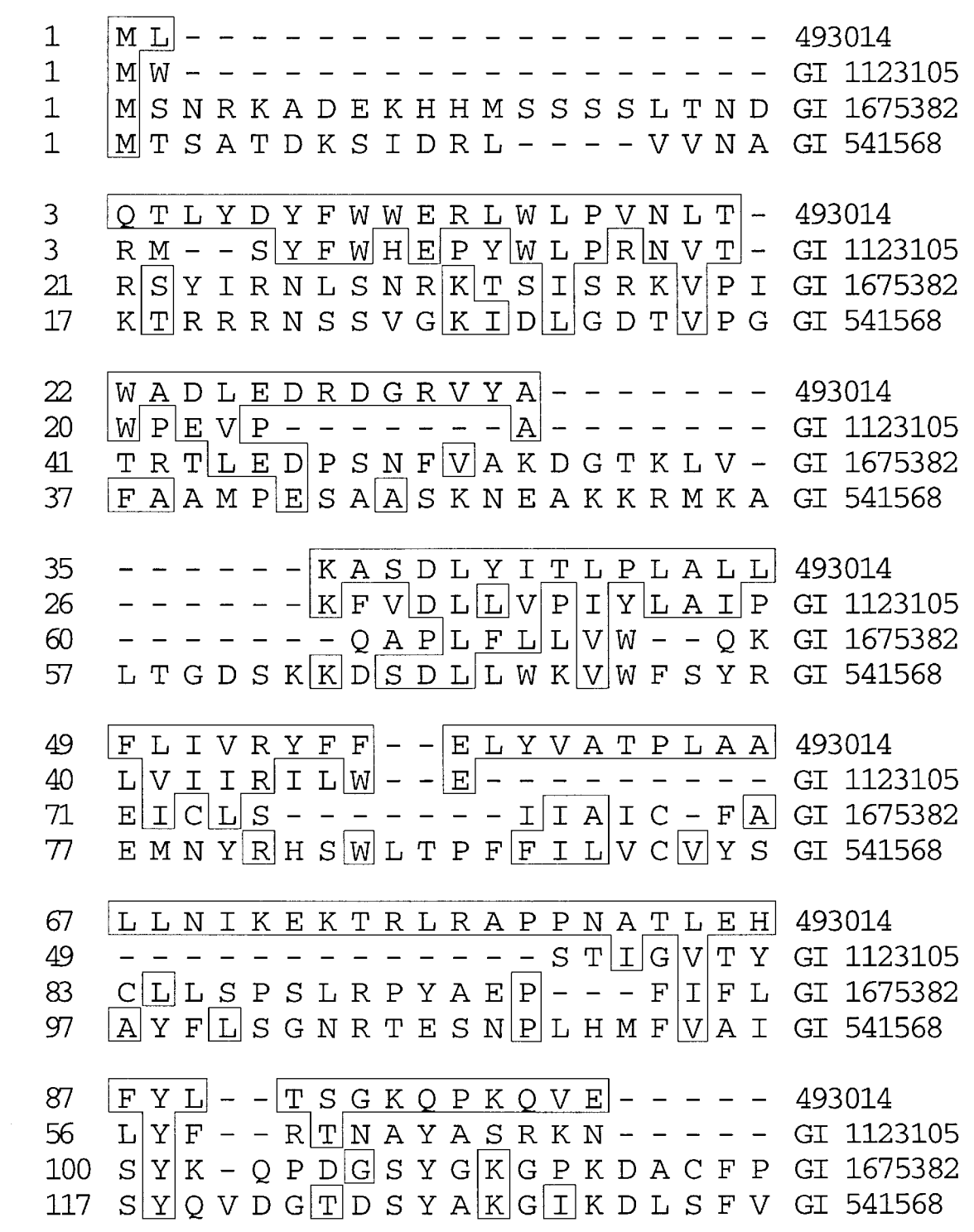
Figure 6B:
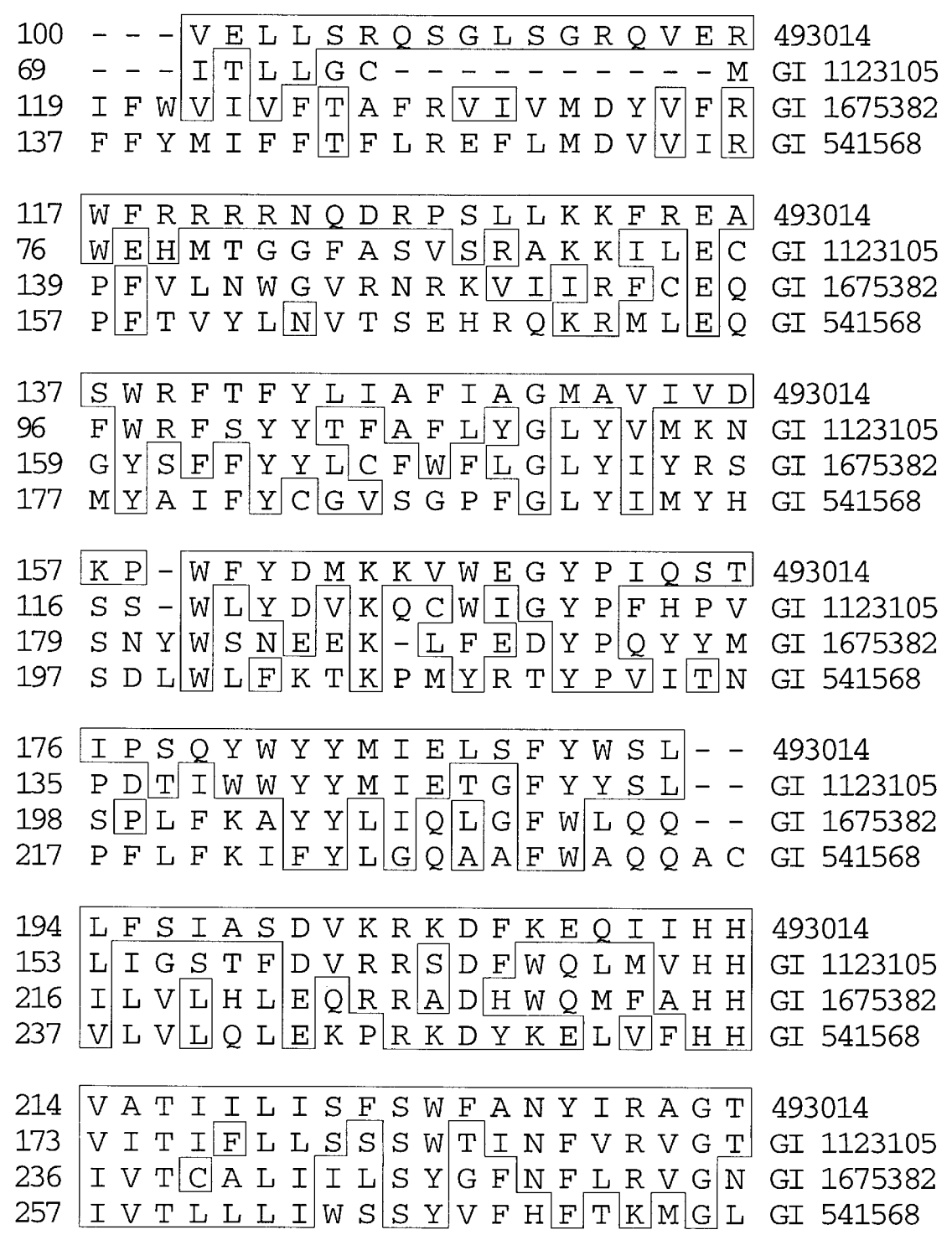
Figure 6C:
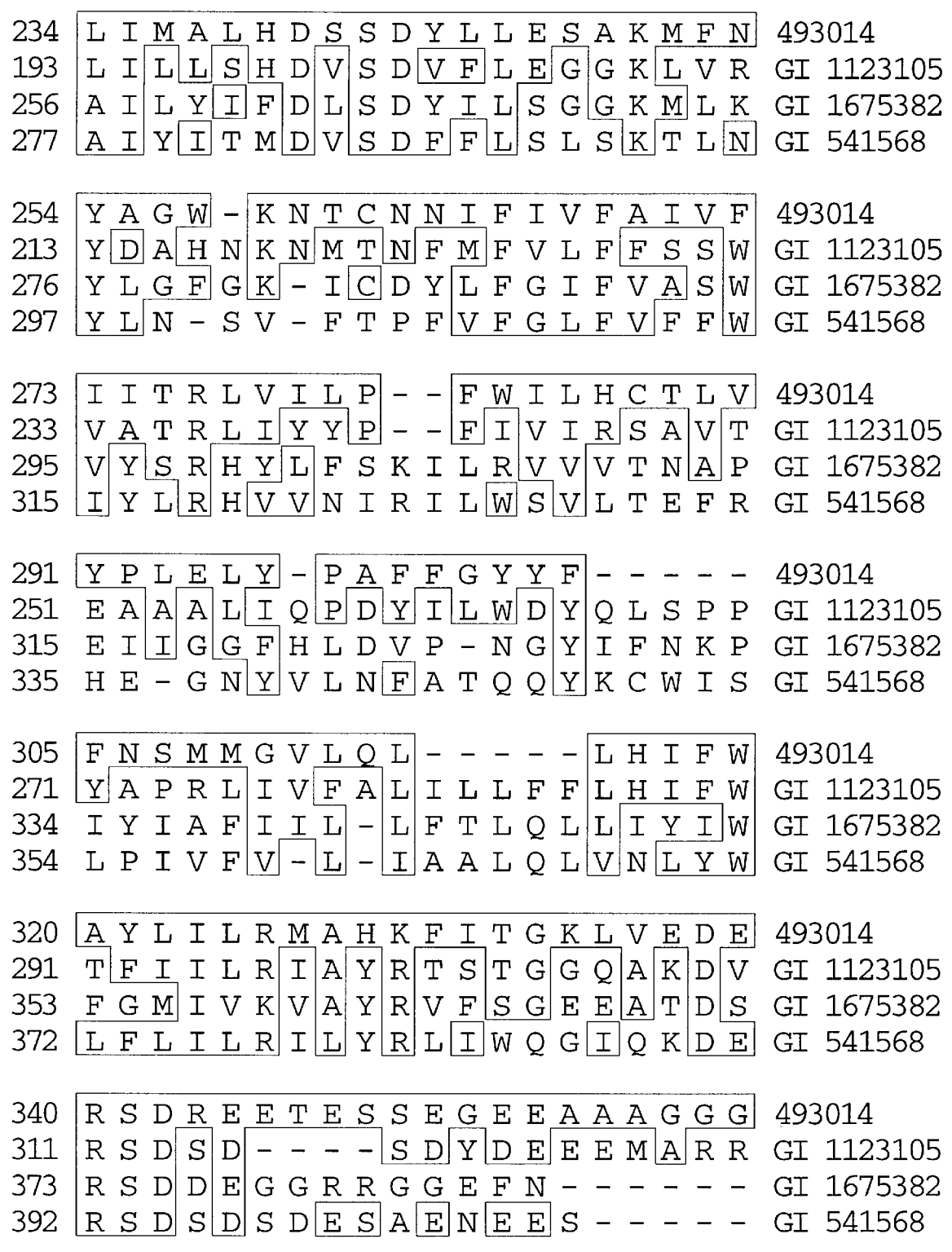
Figure 6D:
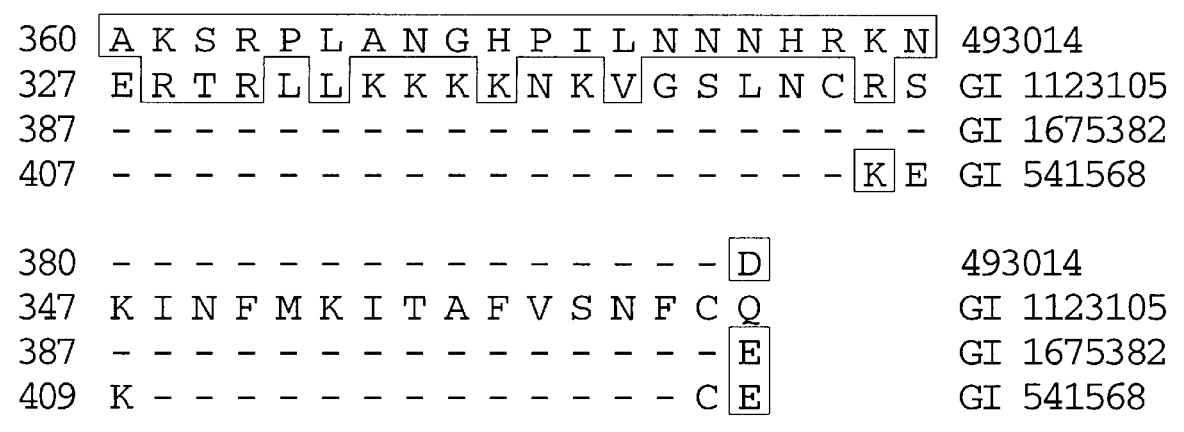

FIGS. 6A, 6B, 6C, and 6D show the amino acid sequence similarity alignments among LAPH-2 (493014; SEQ ID NO:3), C. elegans LAP-1 homolog (GI 1123105; SEQ ID NO:5), longevity assurance factor (LAF) from S. pombe (GI 1675382; SEQ ID NO:6), and LAP-1 from S. cerevisiae (GI 541568; SEQ ID NO:7); aligned amino acids with chemically similar functional groups are boxed.

DESCRIPTION OF THE INVENTION

Figure 7A:
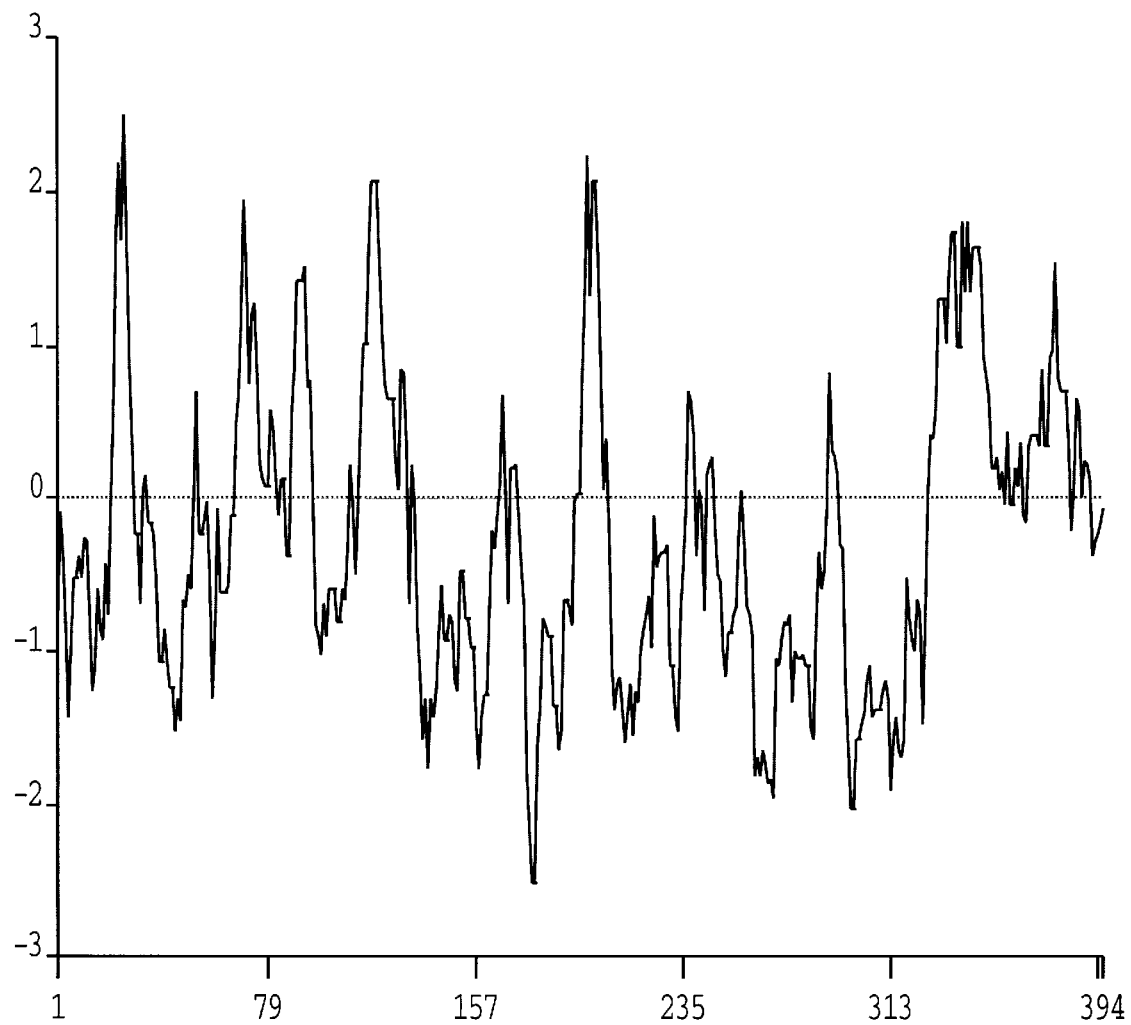
FIGS. 7A and 7B show the hydrophobicity plots for LAPH-1 (SEQ ID NO:1) and LAPH-2 (SEQ ID NO: 3), respectively; the positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

LAPH, as used herein, refers to the amino acid sequences of substantially purified LAPH obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to LAPH, increases or prolongs the duration of the effect of LAPH. Agonists may include proteins, nucleic acids, carbohydrates, or any other molecules which bind to and modulate the effect of LAPH.

An "allele" or "allelic sequence", as used herein, is an alternative form of the gene encoding LAPH. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding LAPH as used herein include those with deletions, insertions, or substitutions of different nucleotides resulting in a polynucleotide that encodes the same or a functionally equivalent LAPH. Included within this definition are polymorphisms which may or may not be readily detectable using a particular oligonucleotide probe of the polynucleotide encoding LAPH, and improper or unexpected hybridization to alleles, with a locus other than the normal chromosomal locus for the polynucleotide sequence encoding LAPH. The encoded protein may also be "altered" and contain deletions, insertions, or substitutions of amino acid residues which produce a silent change and result in a functionally equivalent LAPH. Deliberate amino acid substitutions may be made on the basis of similarity in polarity, charge, solubility, hydrophobicity, hydrophilicity, and/or the amphipathic nature of the residues as long as the biological or immunological activity of LAPH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of LAPH are preferably about 5 to about 15 amino acids in length and retain the biological activity or the immunological activity of LAPH. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to LAPH, decreases the amount or the duration of the effect of the biological or immunological activity of LAPH. Antagonists may include proteins, nucleic acids, carbohydrates, antibodies or any other molecules which decrease the effect of LAPH.

As used herein, the term "antibody" refers to intact molecules as well as fragments thereof, such as Fab, F(ab')$_2$, and Fv, which are capable of binding the epitopic determinant. Antibodies that bind LAPH polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic LAPH, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding LAPH (SEQ ID NO:1 or SEQ ID NO:3) or fragments thereof (e.g., SEQ ID NO:2, SEQ ID NO:4, and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using the XL-PCR kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding LAPH in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to LAPH or the encoded LAPH. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of LAPH. For example, modulation may cause an increase or a decrease in protein activity, binding characteristics, or any other biological, functional or immunological properties of LAPH.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length LAPH-1 and fragments thereof.

The term "sample", as used herein, is used in its broadest sense. A biological sample suspected of containing nucleic acid encoding LAPH, or fragments thereof, or LAPH itself may comprise a bodily fluid, extract from a cell, chromosome, organelle, or membrane isolated from a cell, a cell, genomic DNA, RNA, or cDNA in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of LAPH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of two new human longevity-assurance protein homologs, hereinafter referred to collectively as "LAPH" and individually as "LAPH-1" and "LAPH-2", the polynucleotides encoding LAPH, and the use of these compositions for the diagnosis, prevention, or treatment of disorders associated with dysregulation of cellular homeostasis and disorders associated with aging.

Nucleic acids encoding the LAPH-1 of the present invention were first identified in Incyte Clone 2516821 from the liver tumor cDNA library (LIVRTUT04) using a computer search for amino acid sequence alignments. A consensus sequence, SEQ ID NO:2, was derived from the following overlapping and/or extended nucleic acid sequences: Incyte Clones 1209284 (BRSTNOT02); 1916270 (PROSTUT04); 2188902 (PROSNOT26); 1442622 and 1442407 (THYRNOT03); 2516821 (LIVRTUT04); and 1500224 (SINTBST01).

In one embodiment, the invention encompasses a polypeptide comprising the amino acid sequence of SEQ ID NO:1, as shown in FIGS. 1A, 1B, 1C, and 1D. LAPH-1 is 394 amino acids in length and contains four potential asn-linked glycosylation sites at residues N19, N81, N172 and N364; six potential casein kinase-II phosphorylation sites at residues S4, T21, T23, T288, S342 and S349; and seven potential protein kinase-C phosphorylation sites at residues T74, T114, T130, S137, T174, S294, and T387. LAPH-1 also contains a G-coupled receptor signature sequence pattern comprising residues A46 through L62. As shown in FIGS. 3A, 3B, 3C, and 3D and FIGS. 4A, 4B, 4C, and 4D, LAPH-1 has chemical and structural homology with C. elegans LAP-1 homolog (GI 1123105; SEQ ID NO:5), longevity assurance factor (LAF) from S. pombe (GI 1675382; SEQ ID NO:6), and LAP-1 from S. cerevisiae (GI 541568; SEQ ID NO:7). In particular, LAPH-1 and C. elegans LAP-1 homolog share 52% amino acid sequence similarity and 33% amino acid sequence identity; LAPH-1 and S. pombe LAF share 35% similarity and 22% identity; and LAPH-1 and S. cerevisiae LAP-1 share 33% similarity and 20% identity. Similar amino acids are defined by chemically similar functional groups as described in Karlin, S. et al. (1985; Proc Natl. Acad. Sci. USA 82:8597–8601). As illustrated by FIG. 7A, LAPH-1 contains at least seven potential transmembrane domains. Northern analysis shows the expression of LAPH-I in various tissues, including fetal kidney and lung; cancers of the breast, liver, lung, prostate, small intestine and thyroid; diseased adrenal gland; Crohn's disease-afflicted small intestine; and Alzheimer's disease-afflicted brain tissues (corpus callosum, hippocampus, and pons). The similarity of LAPH-1 to longevity-assurance protein, the presence of multiple phosphorylation sites and a G-coupled receptor signature pattern in the LAPH-1 protein sequence, and the expression of LAPH-1 in diseases associated with dysregulation of cellular homeostasis suggest that LAPH-1 participates in signal transduction and cell cycle regulation, and may play a role in regulating the balance between cell proliferation and apoptosis. Increased expression of LAPH-1 may increase susceptibility to dysregulation of cellular homeostatic pathways.

Nucleic acids encoding the LAPH-2 of the present invention were first identified in Incyte Clone 493014 from a neuronal precursor teratocarcinoma cell line cDNA library (HNT2NOT01) using a computer search for amino acid sequence alignments. A consensus sequence, SEQ ID NO:4, was derived from the following overlapping and/or extended nucleic acid sequences: Incyte Clones 493014 (HNT2NOT01); 503465 (TMLR3DT02); 2512244 (CONUTUT01); 1979181 (LUNGTUT03); 2607554 (LUNGTUT07); 1879756 (LEUKNOT03); 126702 (LUNGNOT01); 1682573 (PROSNOT15); 1361323 (LUNGNOT12); 2733890 (OVARTUT04); 1865737 (PROSNOT19); and 2474414 (SMCANOT01).

Figure 7B:
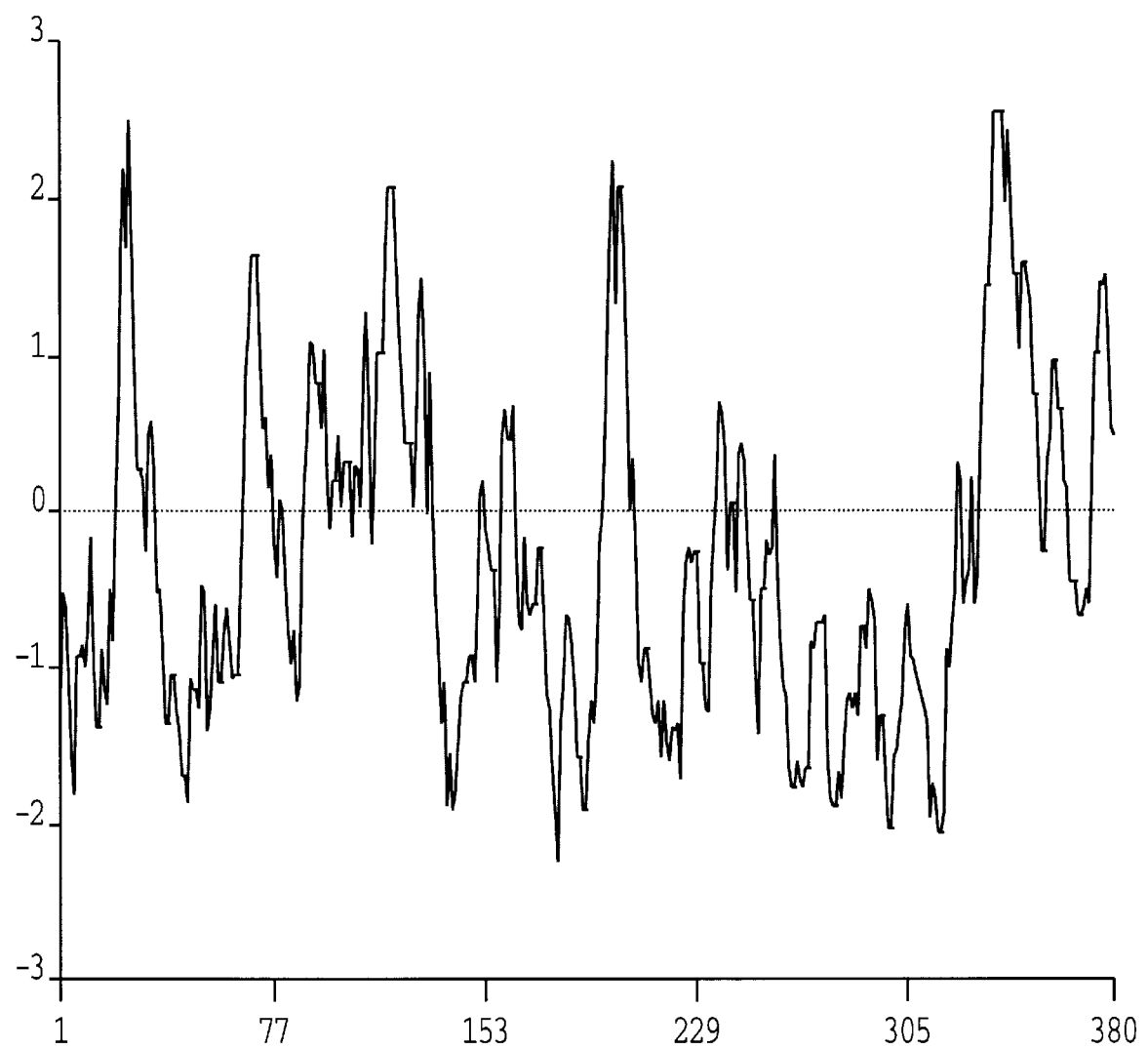

In another embodiment, the invention encompasses a polypeptide comprising the amino acid sequence of SEQ ID NO:3, as shown in FIGS. 2A, 2B, 2C, 2D, 2E and 2F. LAPH-2 is 380 amino acids in length and contains two potential asn-linked glycosylation sites at residues N19 and N81; four potential casein kinase-II phosphorylation sites at residues T4, T21, S341, and S349; and six potential protein kinase-C phosphorylation sites at residues S91, S110, S137, S248, T332, and S341. LAPH-2 also contains an ATP/GTP-binding site P-loop motif comprising residues A355 through S362. As shown in FIGS. 5A, 5B, 5C, and 5D and FIGS. 6A, 6B, 6C, and 6D, LAPH-2 has chemical and structural homology with C. elegans LAP-1 homolog (GI 1123105; SEQ ID NO:5), longevity assurance factor (LAF) from S. pombe (GI 1675382; SEQ ID NO:6), and LAP-1 from S. cerevisiae (GI 541568; SEQ ID NO:7). In particular, LAPH-2 and C. elegans LAP-1 homolog share 49% amino acid sequence similarity and 32% amino acid sequence identity; LAPH-2 and S. pombe LAF share 36% similarity and 19% identity; and LAPH-2 and S. cerevisiae LAP-1 share 34% similarity and 17% identity. Similar amino acids are defined by chemically similar finctional groups as described in Karlin, S. et al. (supra). As illustrated by FIG. 7B, LAPH-2 contains at least seven potential transmembrane domains. Northern analysis shows the expression of LAPH-2 in various libraries, including fibroblast, coronary endothelial, neuronal precursor, cardiac smooth muscle and promonocyte cell lines; fetal colon, liver, kidney, lung and placenta; cancers of the bladder, brain, breast, colon, heart, liver, lung, neuro- and paraganglia, ovary, prostate, testicle, thymus, thyroid and uterus; Alzheimer's disease-afflicted brain; and cells and tissues associated with inflammation or the immune response, including macrophages, bone marrow, lung (asthma), small intestine (Crohn's disease) and skin (erythema nodosum). The similarity of LAPH-2 to longevity-assurance protein, the presence of multiple phosphorylation sites and an ATP/GTP-binding site P-loop motif in the LAPH-2 protein sequence, and the expression of LAPH-2 in diseases and disorders associated with dysregulation of cellular homeostasis suggest that LAPH-2 participates in signal transduction and cell cycle regulation, and may play a role in regulating the balance between cell proliferation and apoptosis. Increased expression of LAPH-2 may increase susceptibility to dysregulation of cellular homeostatic pathways.

The invention also encompasses LAPH variants. A preferred LAPH variant is one having at least 80%, and more preferably at least 90%, amino acid sequence identity to the LAPH amino acid sequence (SEQ ID NO:1 or SEQ ID NO:3) and which retains at least one biological, immunological or other functional characteristic or activity of LAPH. A most preferred LAPH variant is one having at least 95% amino acid sequence identity to SEQ ID NO:1 or SEQ ID NO:3.

The invention also encompasses polynucleotides which encode LAPH. Accordingly, any nucleic acid sequence which encodes the amino acid sequence of LAPH can be used to produce recombinant molecules which express LAPH. In a particular embodiment, the invention encompasses the polynucleotide comprising the nucleic acid sequence of SEQ ID NO:2 as shown in FIGS. 1A, 1B, 1C, and 1D. In another embodiment, the invention encompasses the polynucleotide comprising the nucleic acid sequence of SEQ ID NO:4 as shown in FIGS. 2A, 2B, 2C, 2D, 2E and 2F.

It will be appreciated by those skilled in the art that as a result of the degeneracy of the genetic code, a multitude of nucleotide sequences encoding LAPH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring LAPH, and all such variations are to be considered as being specifically disclosed.

Although nucleotide sequences which encode LAPH and its variants are preferably capable of hybridizing to the nucleotide sequence of the naturally occurring LAPH under appropriately selected conditions of stringency, it may be advantageous to produce nucleotide sequences encoding LAPH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding LAPH and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode LAPH and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding LAPH or any fragment thereof.

Also encompassed by the invention are polynucleotide sequences that are capable of hybridizing to the claimed nucleotide sequences, and in particular, those shown in SEQ ID NO:2 and in SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQVENASE (US Biochemical Corp, Cleveland, Ohio.), Taq polymerase (Perkin Elmer), thermostable T7 polymerase (Amersham, Chicago, Ill.), or combinations of polymerases and proofreading exonucleases such as those found in the ELONGASE amplification system (Gibco/BRL, Gaithersburg, Md.). Preferably, the process is automated with machines such as the Hamilton Micro Lab 2200 (Hamilton, Reno, Nev.), Peltier thermal cycler (PTC200; MJ Research, Watertown, Mass.) and the ABI Catalyst and 373 and 377 DNA sequencers (Perkin Elmer).

The nucleic acid sequences encoding LAPH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode LAPH may be used in recombinant DNA molecules to direct expression of LAPH, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express LAPH.

As will be understood by those of skill in the art, it may be advantageous to produce LAPH-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter LAPH encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding LAPH may be ligated to a heterologous sequence to encode a fusion protein. For example, to screen peptide libraries for inhibitors of LAPH activity, it may be useful to encode a chimeric LAPH protein that can be recognized by a commercially available antibody. A fusion protein may also be engineered to contain a cleavage site located between the LAPH encoding sequence and the heterologous protein sequence, so that LAPH may be cleaved and purified away from the heterologous moiety.

In another embodiment, sequences encoding LAPH may be synthesized, in whole or in part, using chemical methods well known in the art (see Caruthers, M. H. et al. (1980) Nucl. Acids Res. Symp. Ser. 7:215–223, Horn, T. et al. (1980) Nucl. Acids Res. Symp. Ser. 225–232). Alternatively, the protein itself may be produced using chemical methods to synthesize the amino acid sequence of LAPH, or a fragment thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of LAPH, or any part thereof, may be altered during direct synthesis and/or combined using chemical methods with sequences from other proteins, or any part thereof, to produce a variant polypeptide.

In order to express a biologically active LAPH, the nucleotide sequences encoding LAPH or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding LAPH and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding LAPH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding LAPH, vectors based on SV40 or EBV may be used with an appropriate selectable marker.

In bacterial systems, a number of expression vectors may be selected depending upon the use intended for LAPH. For example, when large quantities of LAPH are needed for the induction of antibodies, vectors which direct high level expression of fusion proteins that are readily purified may be used. Such vectors include, but are not limited to, the multifunctional *E. coli* cloning and expression vectors such as the BLUESCRIPT phagemid (Stratagene), in which the sequence encoding LAPH may be ligated into the vector in frame with sequences for the amino-terminal Met and the subsequent 7 residues of β-galactosidase so that a hybrid protein is produced; pIN vectors (Van Heeke, G. and S. M.

Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding LAPH may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express LAPH. For example, in one such system, *Autographa californica* nuclear polyhedrosis virus (AcNPV) is used as a vector to express foreign genes in *Spodoptera frugiperda* cells or in Trichoplusia larvae. The sequences encoding LAPH may be cloned into a non-essential region of the virus, such as the polyhedrin gene, and placed under control of the polyhedrin promoter. Successful insertion of LAPH will render the polyhedrin gene inactive and produce recombinant virus lacking coat protein. The recombinant viruses may then be used to infect, for example, *S. frugiperda* cells or Trichoplusia larvae in which LAPH may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding LAPH may be ligated into an adenovirus transcription/translation complex consisting of the late promoter and tripartite leader sequence. Insertion in a non-essential E1 or E3 region of the viral genome may be used to obtain a viable virus which is capable of expressing LAPH in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding LAPH. Such signals include the ATG initiation codon and adjacent sequences. In cases where sequences encoding LAPH, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express LAPH may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Nati. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding LAPH is inserted within a marker gene sequence, transformed cells containing sequences encoding LAPH can be identified by the absence of marker gene function. Alternatively, a marker gene can be placed in tandem with a sequence encoding LAPH under the control of a single promoter. Expression of the marker gene in response to induction or selection usually indicates expression of the tandem gene as well.

Alternatively, host cells which contain the nucleic acid sequence encoding LAPH and express LAPH may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding LAPH can be detected by DNA-DNA or DNA-RNA hybridization or amplification using probes or fragments or fragments of polynucleotides encoding LAPH. Nucleic acid amplification based assays involve the use of oligonucleotides or oligomers based on the sequences encoding LAPH to detect transformants containing DNA or RNA encoding LAPH.

A variety of protocols for detecting and measuring the expression of LAPH, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on LAPH is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding LAPH include oligolabeling, nick translation, end-labeling or PCR amplification using a labeled nucleotide. Alternatively, the sequences encoding LAPH, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio.). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding LAPH may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode LAPH may be designed to contain signal sequences which direct secretion of LAPH through a prokaryotic or eukaryotic cell membrane. Other constructions may be used to join sequences encoding LAPH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and LAPH may be used to facilitate purification. One such expression vector provides for expression of a fusion protein containing LAPH and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying LAPH from the fusion protein. A discussion of vectors which contain fusion proteins is provided in Kroll, D. J. et al. (1993; DNA Cell Biol. 12:441–453).

In addition to recombinant production, fragments of LAPH may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of LAPH may be chemically synthesized separately and combined using chemical methods to produce the full length molecule.

THERAPEUTICS

Chemical and structural homology exists among LAPH, C. elegans LAP-1 homolog (GI 1123105), S. pombe LAF (GI 1675382), and S. cerevisiae LAP-1 (GI 541568). In addition, LAPH is expressed in tumors, fetal tissues, cell lines, cells and tissues involved in inflammation, and Alzheimer's disease-afflicted brain. Increased expression of LAPH appears to increase susceptibility to dysregulation of cellular homeostatic pathways. Therefore, LAPH appears to play a role in disorders associated with dysregulation of cellular homeostasis and disorders associated with aging.

Therefore, in one embodiment, an antagonist of LAPH may be administered to a subject to prevent or treat a disorder associated with dysregulation of cellular homeostasis. Such disorders include, but are not limited to, cancers such as adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders associated with inflammation or autoimmune disease including AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma; neurodegenerative disorders including akathesia, Alzheimer's disease, amnesia, amyotrophic lateral sclerosis, bipolar disorder, catatonia, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder; and myelodysplastic disorders such as aplastic anemia and pancytopenia. In one aspect, an antibody which specifically binds LAPH may be used directly as an antagonist or indirectly as a targeting or delivery mechanism for bringing a pharmaceutical agent to cells or tissue which express LAPH.

In another embodiment, a vector expressing the complement of the polynucleotide encoding LAPH may be administered to a subject to treat or prevent a disorder associated with dysregulation of cellular homeostasis including, but not limited to, those described above.

In another embodiment, an antagonist of LAPH may be administered to a subject to prevent or treat a disorder associated with aging. Such disorders include, but are not limited to, Alzheimer's disease, Pick's disease, Huntington's disease, Parkinson's disease, myotonic dystrophy, multiple sclerosis, adult onset leukodystrophy, diabetes mellitus, arteriosclerosis, scleroderma, cataract, osteosarcoma, osteoporosis, erythroidmacrocytosis, and premature aging syndromes including Werner's and Okamoto's syndromes. In one aspect, an antibody which specifically binds LAPH may be used directly as an antagonist or indirectly as a targeting or delivery mechanism for bringing a pharmaceutical agent to cells or tissue which express LAPH.

In another embodiment, a vector expressing the complement of the polynucleotide encoding LAPH may be administered to a subject to treat or prevent a disorder associated with aging including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of LAPH may be produced using methods which are generally known in the art. In particular, purified LAPH may be used to produce antibodies or to screen libraries of pharmaceutical agents to identify those which specifically bind LAPH.

Antibodies to LAPH may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with LAPH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to LAPH have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of LAPH amino acids may be fused with those of another protein such as keyhole limpet hemocyanin and antibody produced against the chimeric molecule.

Monoclonal antibodies to LAPH may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce LAPH-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for LAPH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between LAPH and its specific antibody. A two-site, monoclonal-based immunoassay utilizing monoclonal antibodies reactive to two non-interfering LAPH epitopes is preferred, but a competitive binding assay may also be employed (Maddox, supra).

In another embodiment of the invention, the polynucleotides encoding LAPH, or any fragment or complement thereof, may be used for therapeutic purposes. In one aspect, the complement of the polynucleotide encoding LAPH may be used in situations in which it would be desirable to block the transcription of the mRNA. In particular, cells may be transformed with sequences complementary to polynucleotides encoding LAPH. Thus, complementary molecules or fragments may be used to modulate LAPH activity, or to achieve regulation of gene function. Such technology is now well known in the art, and sense or antisense oligonucleotides or larger fragments, can be designed from various locations along the coding or control regions of sequences encoding LAPH.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding LAPH. These techniques are described both in Sambrook et al. (supra) and in Ausubel et al. (supra).

Genes encoding LAPH can be turned off by transforming a cell or tissue with expression vectors which express high levels of a polynucleotide or fragment thereof which encodes LAPH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding LAPH (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding LAPH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding LAPH. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of LAPH, antibodies to LAPH, mimetics, agonists, antagonists, or inhibitors of LAPH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0. 1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of LAPH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example LAPH or fragments thereof, antibodies of LAPH, agonists, antagonists or inhibitors of LAPH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind LAPH may be used for the diagnosis of conditions or diseases characterized by expression of LAPH, or in assays to monitor patients being treated with LAPH, agonists, antagonists or inhibitors. The antibodies useful for diagnostic purposes may be prepared in the same manner as those described above for therapeutics. Diagnostic assays for LAPH include methods which utilize the antibody and a label to detect LAPH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring LAPH are known in the art and provide a basis for diagnosing altered or abnormal levels of LAPH expression. Normal or standard values for LAPH expression are established by combining body fluids or cell extracts taken from normal mammalian subjects, preferably human, with antibody to LAPH under conditions suitable for complex formation The amount of standard complex formation may be quantified by various methods, but preferably by photometric, means. Quantities of LAPH expressed in subject, control and disease, samples from biopsied tissues are compared with the standard values. Deviation between standard and subject values establishes the parameters for diagnosing disease.

In another embodiment of the invention, the polynucleotides encoding LAPH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of LAPH may be correlated with disease. The diagnostic assay may be used to distinguish between absence, presence, and excess expression of LAPH, and to monitor regulation of LAPH levels during therapeutic intervention.

In one aspect, hybridization with PCR probes which are capable of detecting polynucleotide sequences, including genomic sequences, encoding LAPH or closely related molecules, may be used to identify nucleic acid sequences which encode LAPH. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding LAPH, alleles, or related sequences.

Probes may also be used for the detection of related sequences, and should preferably contain at least 50% of the nucleotides from any of the LAPH encoding sequences. The hybridization probes of the subject invention may be DNA or RNA and derived from the nucleotide sequence of SEQ ID NO:2 or SEQ ID NO:4 or from genomic sequence including promoter, enhancer elements, and introns of the naturally occurring LAPH.

Means for producing specific hybridization probes for DNAs encoding LAPH include the cloning of nucleic acid sequences encoding LAPH or LAPH derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding LAPH may be used for the diagnosis of conditions or disorders which are associated with expression of LAPH. Examples of such conditions or disorders include cancers such as adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders associated with inflammation or autoimmune disease including AIDS, Addison's disease, adult respiratory distress syndrome, allergies, anemia, asthma, atherosclerosis, bronchitis, cholecystitis, Crohn's disease, ulcerative colitis, atopic dernatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma; neurodegenerative disorders including akathesia, Alzheimer's disease, amnesia, amyotrophic lateral sclerosis, bipolar disorder, catatonia, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder; myelodysplastic disorders such as aplastic anemia and pancytopenia; and disorders associated with aging including Alzheimer's disease, Pick's disease, Huntington's disease, Parkinson's disease, myotonic dystrophy, multiple sclerosis, adult onset leukodystrophy, diabetes mellitus, arteriosclerosis, scleroderma, cataract, osteosarcoma, osteoporosis, erythroidmacrocytosis, and premature aging syndromes including Werner's and Okamoto's syndromes. The polynucleotide sequences encoding LAPH may be used in Southern or northern analysis, dot blot, or other membrane-based technologies; in PCR technologies; or in dipstick, pin, ELISA assays or microarrays utilizing fluids or tissues from patient biopsies to detect altered LAPH expression. Such qualitative or quantitative methods are well known in the art.

In a particular aspect, the nucleotide sequences encoding LAPH may be useful in assays that detect activation or induction of various cancers, particularly those mentioned above. The nucleotide sequences encoding LAPH may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding LAPH in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of LAPH, a normal or standard profile for expression is established. This may be accomplished by combining body fluids or cell extracts taken from normal subjects, either animal or human, with a sequence, or a fragment thereof, which encodes LAPH, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding LAPH may involve the use of PCR. Such oligomers may be chemically synthesized, generated enzymatically, or produced in vitro. Oligomers will preferably consist of two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of LAPH include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode LAPH may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding LAPH on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, LAPH, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between LAPH and the agent being tested, may be measured.

Another technique for drug screening which may be used provides for high throughput screening of compounds having suitable binding affinity to the protein of interest as described in published PCT application WO84/03564. In this method, as applied to LAPH large numbers of different small test compounds are synthesized on a solid substrate, such as plastic pins or some other surface. The test compounds are reacted with LAPH, or fragments thereof, and washed. Bound LAPH is then detected by methods well known in the art. Purified LAPH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding LAPH specifically compete with a test compound for binding LAPH. In this manner, the antibodies can be used to detect the presence of any peptide which shares one or more antigenic determinants with LAPH.

In additional embodiments, the nucleotide sequences which encode LAPH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

LIVRTUT04

The LIVRTUT04 cDNA library was prepared from cancerous liver tissue obtained from a 50-year-old Caucasian male during a partial hepatectomy. Pathology indicated a grade 3–4 hepatoma forming a mass. Surgical margins were free of tumor. A 1.5 cm cavity of gel foam was present at the capsular surface. No lymphovascular invasion was seen. The adjacent liver showed mild portal fibrosis with lymphoid aggregates and mild steatosis. Patient history included benign hypertension and hepatitis at the age of 16. The patient was classified as a carrier because patient was positive for antibody to hepatitis B core antigen and hepatitis B surface antigen, while negative for HBV DNA.

The frozen tissue was homogenized and lysed in TRIZOL reagent (1 gm tissue/10 ml TRIZOL, Cat. #10296-028; Gibco/BRL), a monophasic solution of phenol and guanidine isothiocyanate, using a Brinkmann POLYTRON homogenizer PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and treated with DNase for 25 min at 37° C. The RNA was re-extracted once with acid phenol-chloroform pH 4.7 and precipitated using 0.3M sodium acetate and 2.5 volumes ethanol. The mRNA was then isolated with the OLIGOTEX kit (QIAGEN, Inc., Chatsworth, Calif.) and used to construct the cDNA library.

The mRNA was handled according to the recommended protocols in the SUPERSCRIPT plasmid system (Cat. #18248-013, Gibco/BRL). LIVRTUT04 cDNAs were fractionated on a SEPHAROSE CL4B column (Cat. #275105-01; Pharmacia & Upjohn), and those cDNAs exceeding 400 bp were ligated into pINCY 1. The plasmid pINCY 1 was subsequently transformed into DH5a competent cells (Cat. #18258-012; Gibco/BRL).

HNT2NOT01

The hNT2 cell line derives from a human teratocarcinoma and exhibits characteristics of a committed neuronal precursor cell at an early stage of development. The HNT2NOT01 cDNA library prepared from this untreated cell line was obtained from Stratagene (Cat. No. 937230). The cDNA library was constructed by essentially the following procedure. cDNAs were primed using oligo d(T) and size fractionated to isolate fragments of 500 bp and larger. Synthetic adapter oligonucleotides were ligated onto the cDNA molecules enabling them to be inserted into the UNIZAP vector system (Stratagene). The quality of the cDNA library was screened using DNA probes, and then, the pBluescript phagemid (Stratagene) was excised. Subsequently, the custom-constructed library phage particles were infected into *E. coli* host strain XL1-BLUE compentent cells (Stratagene).

II Isolation and Sequencing of cDNA Clones

Plasmid or phagemid DNA was purified using the MINIPREP Kit (Catalogue # 77468, Advanced Genetic Technologies Corporation, Gaithersburg Md.), a 96-well block kit with reagents for 960 purifications. The recommended protocol included with the kit was employed except for the following changes. Each of the 96 wells was filled with only 1 ml of sterile Terrific Broth (Catalog # 22711, GIBCO/BRL) with carbenicillin at 25 mg/L and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to Tris buffer was not routinely performed. After the last step in the protocol, samples were transferred to a Beckman 96-well block for storage.

The cDNAs were sequenced by the method of Sanger F. and A. R. Coulson (1975; J Mol Biol 94:441f), using a Hamilton MICROLAB 2200 (Hamilton, Reno Nev.) in combination with four Peltier thermal cyclers (PTC200 from MJ Research, Watertown Mass.) and Applied Biosystems 377 or 373 DNA sequencing systems (Perkin Elmer), and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Altschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\text{\% sequence identity} \times \text{\% maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding LAPH occurs. Abundance and percent abundance are also reported. Abundance directly reflects the number of times a particular transcript is represented in a cDNA library, and percent abundance is abundance divided by the total number of sequences examined in the cDNA library.

V Extension of LAPH Encoding Polynucleotides

The nucleic acid sequence of Incyte Clone 2516821 or of Incyte Clone 493014 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK DNA purification kit (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 or of SEQ ID NO:4 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 primer analysis software (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1 × saline sodium citrate and 0.5% sodium dodecyl sulfate. After XOMAT AR autoradiography film (Kodak, Rochester, N.Y.) is exposed to the blots, or the blots are placed in a PHOS-PHOIMAGER cassette (Molecular Dynamics, Sunnyvale, Calif.) for several hours, hybridization patterns are compared visually.

VII Microarrays

To produce oligonucleotides for a microarray, one of the nucleotide sequences described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the LAPH-encoding sequence, or any part thereof, is used to decrease or inhibit expression of naturally occurring LAPH. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of LAPH, SEQ ID NO:1 or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the LAPH-encoding transcript.

IX Expression of LAPH

Expression of LAPH is accomplished by subcloning the cDNAs into appropriate vectors and transforming the vectors into host cells. In this case, the cloning vector is also used to express LAPH in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein.

X Demonstration of LAPH Activity

The effect of LAPH on apoptosis may be assayed by quantitating apoptosis-associated DNA fragmentation using the FLUORESCEIN APOPTOSIS DETECTION SYSTEM (Catalog #G3250, Promega). This kit utilizes the terminal deoxynucleotidyl transferase (TdT)-mediated dUTP nick end-labeling (TUNEL) technique.

PC 12 cells cultured in the presence of 100 ng/ml nerve growth factor (NGF) for at least 2 weeks undergo apoptosis within 48 hours once NGF is removed from the culture medium (Wolozin, B. et al. (1996) Science 274:1710–1713). PC12 cells cultured in the presence of NGF are transfected with a eukaryotic expression vector encoding LAPH or with the vector alone. Cells are cultured for 48 hours in the presence or absence of NGF. Apoptosis is assayed by the incorporation of fluorescein-12-dUTP at the 3'-hydroxyl ends of fragmented DNA according to the directions supplied by Promega. Cells harboring fluorescein-dUTP-labeled DNA are visualized directly by fluorescence microscopy or quantitated by fluorescence activated cell sorting (FACS).

XI Production of LAPH Specific Antibodies

LAPH that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using DNAS-TAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring LAPH
Using Specific Antibodies

Naturally occurring or recombinant LAPH is substantially purified by immunoaffinity chromatography using antibodies specific for LAPH. An immunoaffinity column is constructed by covalently coupling LAPH antibody to an activated chromatographic resin, such as CNBr-activated SEPHAROSE (Pharmacia & Upjohn). After the coupling, the resin is blocked and washed according to the manufacturer's instructions.

Media containing LAPH is passed over the immunoaffinity column, and the column is washed under conditions that allow the preferential absorbance of LAPH (e.g., high ionic strength buffers in the presence of detergent). The column is eluted under conditions that disrupt antibody/LAPH binding (eg, a buffer of pH 2–3 or a high concentration of a chaotrope, such as urea or thiocyanate ion), and LAPH is collected.

XIII Identification of Molecules Which Interact with LAPH

LAPH or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled LAPH, washed and any wells with labeled LAPH complex are assayed. Data obtained using different concentrations of LAPH are used to calculate values for the number, affinity, and association of LAPH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising the amino acid sequence of SEO ID NO:1.

2. A composition comprising the polynucleotide of claim 1.

3. An isolated and purified polynucleotide which is fully complementary to the polynucleotide of claim 1.

4. An isolated and purified polynucleotide comprising SEQ ID NO:2.

5. An isolated and purified polynucleotide which is fully complementary to the polynucleotide of claim 4.

6. An expression vector comprising the polynucleotide of claim 1.

7. A host cell comprising the expression vector of claim 6.

8. A method for producing a polypeptide comprising the amino acid sequence of SEQ ID NO:1, the method comprising the steps of:
   a) culturing the host cell of claim 7 under conditions suitable for the expression of the polypeptide; and
   b) recovering the polypeptide from the host cell culture.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 394 amino acids
        (B) TYPE: amino acid
        (C) STRANDEDNESS: single
        (D) TOPOLOGY: linear (vii) IMMEDIATE SOURCE:
        (A) LIBRARY: LIVRTUT04
        (B) CLONE: 2516821

(xi) SEQUENCE DESCRIPTION: SEQ ID NO:1:

Met Leu Ser Ser Phe Asn Glu Trp Phe Trp Gln Asp Arg Phe Trp Leu
1               5                   10                  15

Pro Pro Asn Val Thr Trp Thr Glu Leu Glu Asp Arg Asp Gly Arg Val
            20                  25                  30

Tyr Pro His Pro Gln Asp Leu Leu Ala Ala Leu Pro Leu Ala Leu Val
        35                  40                  45

Leu Leu Ala Met Arg Leu Ala Phe Glu Arg Phe Ile Gly Leu Pro Leu
    50                  55                  60

Ser Arg Trp Leu Gly Val Arg Asp Gln Thr Arg Arg Gln Val Lys Pro
65                  70                  75                  80

Asn Ala Thr Leu Glu Lys His Phe Leu Thr Glu Gly His Arg Pro Lys
                85                  90                  95

Glu Pro Gln Leu Ser Leu Leu Ala Ala Gln Cys Gly Leu Thr Leu Gln
            100                 105                 110

Gln Thr Gln Arg Trp Phe Arg Arg Arg Asn Gln Asp Arg Pro Gln
            115                 120                 125

Leu Thr Lys Lys Phe Cys Glu Ala Ser Trp Arg Phe Leu Phe Tyr Leu
    130                 135                 140

```
Ser Ser Phe Val Gly Gly Leu Ser Val Leu Tyr His Glu Ser Trp Leu
145                 150                 155                 160

Trp Ala Pro Val Met Cys Trp Asp Arg Tyr Pro Asn Gln Thr Leu Lys
            165                 170                 175

Pro Ser Leu Tyr Trp Trp Tyr Leu Leu Glu Leu Gly Phe Tyr Leu Ser
            180                 185                 190

Leu Leu Ile Arg Leu Pro Phe Asp Val Lys Arg Lys Asp Phe Lys Glu
            195                 200                 205

Gln Val Ile His His Phe Val Ala Val Ile Leu Met Thr Phe Ser Tyr
            210                 215                 220

Ser Ala Asn Leu Leu Arg Ile Gly Ser Leu Val Leu Leu Leu His Asp
225                 230                 235                 240

Ser Ser Asp Tyr Leu Leu Glu Ala Cys Lys Met Val Asn Tyr Met Gln
                245                 250                 255

Tyr Gln Gln Val Cys Asp Ala Leu Phe Leu Ile Phe Ser Phe Val Phe
                260                 265                 270

Phe Tyr Thr Arg Leu Val Leu Phe Pro Thr Gln Ile Leu Tyr Thr Thr
            275                 280                 285

Tyr Tyr Glu Ser Ile Ser Asn Arg Gly Pro Phe Phe Gly Tyr Tyr Phe
            290                 295                 300

Phe Asn Gly Leu Leu Met Leu Leu Gln Leu Leu His Val Phe Trp Ser
305                 310                 315                 320

Cys Leu Ile Leu Arg Met Leu Tyr Ser Phe Met Lys Lys Gly Gln Met
                325                 330                 335

Glu Lys Asp Ile Arg Ser Asp Val Glu Glu Ser Asp Ser Ser Glu Glu
                340                 345                 350

Ala Ala Ala Ala Gln Glu Pro Leu Gln Leu Lys Asn Gly Thr Ala Gly
            355                 360                 365

Gly Pro Arg Pro Ala Pro Thr Asp Gly Pro Arg Ser Arg Val Ala Gly
            370                 375                 380

Arg Leu Thr Asn Arg His Thr Thr Ala Thr
385                 390
```

(2) INFORMATION FOR SEQ ID NO:2:

(i) SEQUENCE CHARACTERISTICS:
        (A) LENGTH: 1547 base pairs
        (B) TYPE: nucleic acid
        (C) STRANDEDNESS: single
        (D) TOPOLOGY: linear (xi) SEQUENCE DESCRIPTION: SEQ ID NO:2:

```
CTTTCCTTAC CTGTTTTTCC AGCTCACCCA CTGCCAGCAG AGAATGCTGT CCAGTTTCAA      60

CGAGTGGTTT TGGCAGGACA GGTTCTGGTT ACCACCCAAT GTCACGTGGA CAGAGCTAGA     120

AGACCGGGAT GGCCGTGTCT ACCCCCACCC CCAGGACTTG TTGGCAGCCC TGCCCCTGGC     180

GCTGGTCCTC CTGGCCATGC GCCTTGCCTT TGAGAGATTC ATTGGCCTGC CCCTGAGCCG     240

GTGGCTGGGT GTGAGGGATC AGACCAGGAG GCAAGTGAAG CCCAACGCCA CGCTGGAGAA     300

ACACTTCCTC ACGGAAGGGC ACAGGCCCAA GGAGCCCCAG CTGTCTCTCC TGGCCGCCCA     360

GTGTGGCCTC ACGCTGCAGC AGACCCAGCG ATGGTTCCGG AGACGCCGGA ACCAGGATCG     420

ACCCCAGCTG ACCAAGAAGT CTGTGAGGC CAGCTGGAGG TTTCTCTTCT ACCTGTCCTC     480

CTTCGTGGGC GGCTCTCGG TCCTGTACCA CGAGTCATGG CTGTGGGCAC CAGTAATGTG     540

CTGGGACAGG TACCCAAACC AGACTCTGAA GCCATCCCTG TACTGGTGGT ACCTCTTGGA     600
```

-continued

```
GCTGGGTTTC TACCTCTCAC TGCTAATCAG GCTGCCCTTT GATGTCAAGC GCAAGGATTT      660

CAAGGAGCAG GTGATACACC ACTTCGTGGC GGTCATCCTG ATGACCTTCT CCTACAGTGC      720

CAACCTGCTG CGCATTGGCT CTCTGGTGCT GCTGTTACAC GATTCCTCTG ACTACCTGCT      780

GGAGGCCTGT AAGATGGTCA ACTACATGCA GTATCAGCAA GTGTGCGACG CTCTCTTCCT      840

CATCTTCTCC TTTGTCTTCT TCTACACCCG ACTGGTCCTC TTTCCCACCC AGATCCTCTA      900

CACCACATAC TACGAGTCCA TCAGCAACAG GGGCCCCTTC TTCGGCTACT ACTTCTTCAA      960

CGGGCTTCTG ATGTTGCTGC AGCTGCTGCA CGTGTTCTGG TCTTGCCTCA TTCTGCGCAT     1020

GCTCTATAGC TTCATGAAGA AGGGCCAGAT GGAGAAGGAC ATTCGTAGTG ATGTAGAAGA     1080

ATCAGACTCC AGTGAGGAGG CGGCGGCGGC CCAGGAACCT CTGCAGCTAA GAACGGGAC     1140

AGCTGGAGGG CCCAGGCCAG CCCCCACTGA TGGCCCTCGG AGCCGGGTGG CCGGGCGTCT     1200

GACCAACAGG CACACAACAG CCACATAGCC GGGCGGGGCT GGCTGTAAGG GGTTGCCCCC     1260

CCGCCAGTGC CTTGGATATT TCTGGGGTGA CTGGACTGGC GCCCCTGGGC CACCTTTCTG     1320

GAGACAGGGA GGGCCCCACC CGGGGTGGGT GGGAAGGCTG ATGATCTGTC TCCAGCCCCT     1380

TCCTTCTGCC CACCCGCCCT TCTTCCCTCT GGGCAACTGG ACAGATCTGG GAGCCAGCAG     1440

CTGGATGCTG TGGCTGGCCA GAGACACCTC CAGGCTGTAG CCTGGGGGCT GGGGGGAGCC     1500

CCAGGCTGAA AAGGGTCCAA TTAAAACAAA TGGAGCCAAA AAAAGAA                   1547
```

(2) INFORMATION FOR SEQ ID NO:3:

(i) SEQUENCE CHARACTERISTICS:
        (A) LENGTH: 380 amino acids
        (B) TYPE: amino acid
        (C) STRANDEDNESS: single
        (D) TOPOLOGY: linear (vii) IMMEDIATE SOURCE:
        (A) LIBRARY: HNT2NOT01
        (B) CLONE: 493014

(xi) SEQUENCE DESCRIPTION: SEQ ID NO:3:

```
Met Leu Gln Thr Leu Tyr Asp Tyr Phe Trp Trp Glu Arg Leu Trp Leu
 1               5                  10                  15

Pro Val Asn Leu Thr Trp Ala Asp Leu Glu Asp Arg Asp Gly Arg Val
            20                  25                  30

Tyr Ala Lys Ala Ser Asp Leu Tyr Ile Thr Leu Pro Leu Ala Leu Leu
        35                  40                  45

Phe Leu Ile Val Arg Tyr Phe Phe Glu Leu Tyr Val Ala Thr Pro Leu
    50                  55                  60

Ala Ala Leu Leu Asn Ile Lys Glu Lys Thr Arg Leu Arg Ala Pro Pro
65                  70                  75                  80

Asn Ala Thr Leu Glu His Phe Tyr Leu Thr Ser Gly Lys Gln Pro Lys
                85                  90                  95

Gln Val Glu Val Glu Leu Leu Ser Arg Gln Ser Gly Leu Ser Gly Arg
            100                 105                 110

Gln Val Glu Arg Trp Phe Arg Arg Arg Asn Gln Asp Arg Pro Ser
        115                 120                 125

Leu Leu Lys Lys Phe Arg Glu Ala Ser Trp Arg Phe Thr Phe Tyr Leu
    130                 135                 140

Ile Ala Phe Ile Ala Gly Met Ala Val Ile Val Asp Lys Pro Trp Phe
145                 150                 155                 160

Tyr Asp Met Lys Lys Val Trp Glu Gly Tyr Pro Ile Gln Ser Thr Ile
                165                 170                 175
```

```
Pro Ser Gln Tyr Trp Tyr Tyr Met Ile Glu Leu Ser Phe Tyr Trp Ser
            180                 185                 190

Leu Leu Phe Ser Ile Ala Ser Asp Val Lys Arg Lys Asp Phe Lys Glu
            195                 200                 205

Gln Ile Ile His His Val Ala Thr Ile Ile Leu Ile Ser Phe Ser Trp
    210                 215                 220

Phe Ala Asn Tyr Ile Arg Ala Gly Thr Leu Ile Met Ala Leu His Asp
225                 230                 235                 240

Ser Ser Asp Tyr Leu Leu Glu Ser Ala Lys Met Phe Asn Tyr Ala Gly
                245                 250                 255

Trp Lys Asn Thr Cys Asn Asn Ile Phe Ile Val Phe Ala Ile Val Phe
                260                 265                 270

Ile Ile Thr Arg Leu Val Ile Leu Pro Phe Trp Ile Leu His Cys Thr
            275                 280                 285

Leu Val Tyr Pro Leu Glu Leu Tyr Pro Ala Phe Phe Gly Tyr Tyr Phe
    290                 295                 300

Phe Asn Ser Met Met Gly Val Leu Gln Leu Leu His Ile Phe Trp Ala
305                 310                 315                 320

Tyr Leu Ile Leu Arg Met Ala His Lys Phe Ile Thr Gly Lys Leu Val
                325                 330                 335

Glu Asp Glu Arg Ser Asp Arg Glu Glu Thr Glu Ser Ser Glu Gly Glu
                340                 345                 350

Glu Ala Ala Ala Gly Gly Gly Ala Lys Ser Arg Pro Leu Ala Asn Gly
            355                 360                 365

His Pro Ile Leu Asn Asn Asn His Arg Lys Asn Asp
    370                 375                 380

(2) INFORMATION FOR SEQ ID NO:4:

(i) SEQUENCE CHARACTERISTICS:
        (A) LENGTH: 2160 base pairs
        (B) TYPE: nucleic acid
        (C) STRANDEDNESS: single
        (D) TOPOLOGY: linear (vii) IMMEDIATE SOURCE:
        (A) LIBRARY: HNT2NOT01
        (B) CLONE: 493014

(xi) SEQUENCE DESCRIPTION: SEQ ID NO:4:

AGGGAGGAGA GGCGCGGGGA GCCAGGCCTC GGGGCCTCGG AGCAACCACC CGAGCAGACG      60

GAGTACACGG AGCAGCGGCC CCGGCCCCGC CAACGCTGCC GCCGGGATGC TCCAGACCTT     120

GTATGATTAC TTCTGGTGGG AACGTCTGTG GCTGCCTGTG AACTTGACCT GGGCCGATCT     180

AGAAGACCGA GATGGACGTG TCTACGCCAA AGCCTCAGAT CTCTATATCA CGCTGCCCCT     240

GGCCTTGCTC TTCCTCATCG TTCGATACTT CTTTGAGCTG TACGTGGCTA CACCACTGGC     300

TGCCCTTTTG AACATAAAGG AGAAAACTCG GCTGCGGGCA CCTCCCAACG CCACCTTGGA     360

ACATTTCTAC CTGACCAGTG GCAAGCAGCC CAAGCAGGTG GAAGTAGAGC TTTTGTCCCG     420

GCAGAGCGGG CTCTCTGGCC GCCAGGTAGA GCGTTGGTTC CGTCGCCGCC GCAACCAGGA     480

CCGGCCCAGT CTCCTCAAGA AGTTCCGAGA AGCCAGCTGG AGATTCACAT TTTACCTGAT     540

TGCCTTCATT GCCGGCATGG CCGTCATTGT GGATAAACCC TGGTTCTATG ACATGAAGAA     600

AGTTTGGGAG GGATATCCCA TACAGAGCAC TATCCCTTCC CAGTATTGGT ACTACATGAT     660

TGAACTTTCC TTCTACTGGT CCCTGCTCTT CAGCATTGCC TCTGATGTCA AGCGAAAGGA     720

TTTCAAGGAA CAGATCATCC ACCATGTGGC CACCATCATT CTCATCAGCT TTCCTGGTT      780
```

```
TGCCAATTAC ATCCGAGCTG GGACTCTAAT CATGGCTCTG CATGACTCTT CCGATTACCT    840

GCTGGAGTCA GCCAAGATGT TTAACTACGC GGGATGGAAG AACACCTGCA ACAACATCTT    900

CATCGTCTTC GCCATTGTTT TTATCATCAC CCGACTGGTC ATCCTGCCCT TCTGGATCCT    960

GCATTGCACC CTGGTGTACC CACTGGAGCT CTATCCTGCC TTCTTTGGCT ATTACTTCTT   1020

CAATTCCATG ATGGGAGTTC TACAGCTGCT GCATATCTTC TGGGCCTACC TCATTTTGCG   1080

CATGGCCCAC AAGTTCATAA CTGGAAAGCT GGTAGAAGAT GAACGCAGTG ACCGGGAAGA   1140

AACAGAGAGC TCAGAGGGGG AGGAGGCTGC AGCTGGGGGA GGAGCAAAGA GCCGGCCCCT   1200

AGCCAATGGC CACCCCATCC TCAATAACAA CCATCGTAAG AATGACTGAA CCATTATTCC   1260

AGCTGCCTCC CAGATTAATG CATAAAGCCA AGGAACTACC CCGCTCCCTG CGCTATAGGG   1320

TCACTTTAAG CTCTGGGGAA AAAGGAGAAA GTGAGAGGAG AGTTCTCTGC ATCCTCCCTC   1380

CTTGCTTGTC ACCCAGTTGC CTTTAAACCA AATTCTAACC AGCCTATCCC CAGGTAGGGG   1440

GACGTTGGTT ATATTCTGTT AGAGGGGAC GGTCGTATTT TCCTCCCTAC CCGCCAAGTC    1500

ATCCTTTCTA CTGCTTTTGA GGCCCTCCCT CAGCTCTCTG TGGGTAGGGG TTACAATTCA   1560

CATTCCTTAT TCTGAGAATT TGGCCCCAGC TGTTTGCCTT TGACTCCCTG ACCTCCAGAG   1620

CCAGGGTTGT GCCTTATTGT CCCATCTGTG GGCCTCATTC TGCCAAAGCT GGACCAAGGC   1680

TAACCTTTCT AAGCTCCCTA ACTTGGGCCA GAAACCAAAG CTGAGCTTTT AACTTTCTCC   1740

CTCTATGACA CAAATGAATT GAGGGTAGGA GGAGGGTGCA CATAACCCTT ACCCTACCTC   1800

TGCCAAAAAG TGGGGCTGT ACTGGGGACT GCTCGGATGA TCTTTCTTAG TGCTACTTCT    1860

TTCAGCTGTC CCTGTAGCGA CAGGTCTAAG ATCTGACTGC CTCCTCCTTT CTCTGGCCTC   1920

TTCCCCCTTC CCTCTTCTCT TCAGCTAGGC TAGCTGGTTT GGAGTAGAAT GGCAACTAAT   1980

TCTAATTTTT ATTTATTAAA TATTTGGGGT TTTGGTTTTA AAGCCAGAAT TACGGCTAGC   2040

ACCTAGCATT TCAGCAGAGG GACCATTTTA GACCAAAATG TACTGTTAAT GGGTTTTTTT   2100

TTAAAATTAA AAGATTAAAT AAAAAATATT AAAAAAAAAA AAAAAAAAA AGGGGGGGGG    2160

(2) INFORMATION FOR SEQ ID NO:5:

(i) SEQUENCE CHARACTERISTICS:
        (A) LENGTH: 362 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1123105

(xi) SEQUENCE DESCRIPTION: SEQ ID NO:5:

Met Trp Arg Met Ser Tyr Phe Trp His Glu Pro Tyr Trp Leu Pro Arg
 1               5                  10                  15

Asn Val Thr Trp Pro Glu Val Pro Ala Lys Phe Val Asp Leu Leu Val
             20                  25                  30

Pro Ile Tyr Leu Ala Ile Pro Leu Val Ile Ile Arg Ile Leu Trp Glu
         35                  40                  45

Ser Thr Ile Gly Val Thr Tyr Leu Tyr Phe Arg Thr Asn Ala Tyr Ala
     50                  55                  60

Ser Arg Lys Asn Ile Thr Leu Leu Gly Cys Met Trp Glu His Met Thr
65                  70                  75                  80

Gly Gly Phe Ala Ser Val Ser Arg Ala Lys Lys Ile Leu Glu Cys Phe
                 85                  90                  95

Trp Arg Phe Ser Tyr Tyr Thr Phe Ala Phe Leu Tyr Gly Leu Tyr Val
```

```
                    100                 105                 110
Met Lys Asn Ser Ser Trp Leu Tyr Asp Val Lys Gln Cys Trp Ile Gly
            115                 120                 125

Tyr Pro Phe His Pro Val Pro Asp Thr Ile Trp Trp Tyr Tyr Met Ile
        130                 135                 140

Glu Thr Gly Phe Tyr Tyr Ser Leu Leu Ile Gly Ser Thr Phe Asp Val
145                 150                 155                 160

Arg Arg Ser Asp Phe Trp Gln Leu Met Val His His Val Ile Thr Ile
                165                 170                 175

Phe Leu Leu Ser Ser Ser Trp Thr Ile Asn Phe Val Arg Val Gly Thr
            180                 185                 190

Leu Ile Leu Leu Ser His Asp Val Ser Asp Val Phe Leu Glu Gly Gly
        195                 200                 205

Lys Leu Val Arg Tyr Asp Ala His Asn Lys Asn Met Thr Asn Phe Met
210                 215                 220

Phe Val Leu Phe Phe Ser Ser Trp Val Ala Thr Arg Leu Ile Tyr Tyr
225                 230                 235                 240

Pro Phe Ile Val Ile Arg Ser Ala Val Thr Glu Ala Ala Leu Ile
                245                 250                 255

Gln Pro Asp Tyr Ile Leu Trp Asp Tyr Gln Leu Ser Pro Pro Tyr Ala
            260                 265                 270

Pro Arg Leu Ile Val Phe Ala Leu Ile Leu Leu Phe Phe Leu His Ile
        275                 280                 285

Phe Trp Thr Phe Ile Ile Leu Arg Ile Ala Tyr Arg Thr Ser Thr Gly
290                 295                 300

Gly Gln Ala Lys Asp Val Arg Ser Asp Ser Asp Ser Asp Tyr Asp Glu
305                 310                 315                 320

Glu Glu Met Ala Arg Arg Glu Arg Thr Arg Leu Leu Lys Lys Lys
                325                 330                 335

Asn Lys Val Gly Ser Leu Asn Cys Arg Ser Lys Ile Asn Phe Met Lys
            340                 345                 350

Ile Thr Ala Phe Val Ser Asn Phe Cys Gln
        355                 360

(2) INFORMATION FOR SEQ ID NO:6:

(i) SEQUENCE CHARACTERISTICS:
        (A) LENGTH: 387 amino acids
        (B) TYPE: amino acid
        (C) STRANDEDNESS: single
        (D) TOPOLOGY: linear (vi) ORIGINAL SOURCE:
        (E) HAPLOTYPE: GenBank (vii) IMMEDIATE SOURCE:
        (A) LIBRARY: 1675382

(xi) SEQUENCE DESCRIPTION: SEQ ID NO:6:

Met Ser Asn Arg Lys Ala Asp Glu Lys His His Met Ser Ser Ser Ser
 1               5                  10                  15

Leu Thr Asn Asp Arg Ser Tyr Ile Arg Asn Leu Ser Asn Arg Lys Thr
            20                  25                  30

Ser Ile Ser Arg Lys Val Pro Ile Thr Arg Thr Leu Glu Asp Pro Ser
        35                  40                  45

Asn Phe Val Ala Lys Asp Gly Thr Lys Leu Val Gln Ala Pro Leu Phe
    50                  55                  60

Leu Leu Val Trp Gln Lys Glu Ile Cys Leu Ser Ile Ile Ala Ile Cys
```

```
            65                  70                  75                  80
    Phe Ala Cys Leu Leu Ser Pro Ser Leu Arg Pro Tyr Ala Glu Pro Phe
                        85                  90                  95
    Ile Phe Leu Ser Tyr Lys Gln Pro Asp Gly Ser Tyr Gly Lys Gly Pro
                       100                 105                 110
    Lys Asp Ala Cys Phe Pro Ile Phe Trp Val Ile Val Phe Thr Ala Phe
                       115                 120                 125
    Arg Val Ile Val Met Asp Tyr Val Phe Arg Pro Phe Val Leu Asn Trp
                       130                 135                 140
    Gly Val Arg Asn Arg Lys Val Ile Ile Arg Phe Cys Glu Gln Gly Tyr
    145                 150                 155                 160
    Ser Phe Phe Tyr Tyr Leu Cys Phe Trp Phe Leu Gly Leu Tyr Ile Tyr
                       165                 170                 175
    Arg Ser Ser Asn Tyr Trp Ser Asn Glu Glu Lys Leu Phe Glu Asp Tyr
                       180                 185                 190
    Pro Gln Tyr Tyr Met Ser Pro Leu Phe Lys Ala Tyr Tyr Leu Ile Gln
                       195                 200                 205
    Leu Gly Phe Trp Leu Gln Gln Ile Leu Val Leu His Leu Glu Gln Arg
                       210                 215                 220
    Arg Ala Asp His Trp Gln Met Phe Ala His His Ile Val Thr Cys Ala
    225                 230                 235                 240
    Leu Ile Ile Leu Ser Tyr Gly Phe Asn Phe Leu Arg Val Gly Asn Ala
                       245                 250                 255
    Ile Leu Tyr Ile Phe Asp Leu Ser Asp Tyr Ile Leu Ser Gly Gly Lys
                       260                 265                 270
    Met Leu Lys Tyr Leu Gly Phe Gly Lys Ile Cys Asp Tyr Leu Phe Gly
                       275                 280                 285
    Ile Phe Val Ala Ser Trp Val Tyr Ser Arg His Tyr Leu Phe Ser Lys
                       290                 295                 300
    Ile Leu Arg Val Val Val Thr Asn Ala Pro Glu Ile Ile Gly Gly Phe
    305                 310                 315                 320
    His Leu Asp Val Pro Asn Gly Tyr Ile Phe Asn Lys Pro Ile Tyr Ile
                       325                 330                 335
    Ala Phe Ile Ile Leu Leu Phe Thr Leu Gln Leu Leu Ile Tyr Ile Trp
                       340                 345                 350
    Phe Gly Met Ile Val Lys Val Ala Tyr Arg Val Phe Ser Gly Glu Glu
                       355                 360                 365
    Ala Thr Asp Ser Arg Ser Asp Asp Glu Gly Gly Arg Arg Gly Gly Glu
                       370                 375                 380
    Phe Asn Glu
    385

(2) INFORMATION FOR SEQ ID NO:7:

(i) SEQUENCE CHARACTERISTICS:
        (A) LENGTH: 411 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 541568

(xi) SEQUENCE DESCRIPTION: SEQ ID NO:7:

Met Thr Ser Ala Thr Asp Lys Ser Ile Asp Arg Leu Val Val Asn Ala
1                   5                  10                  15
```

-continued

```
Lys Thr Arg Arg Arg Asn Ser Ser Val Gly Lys Ile Asp Leu Gly Asp
         20                  25                  30

Thr Val Pro Gly Phe Ala Ala Met Pro Glu Ser Ala Ala Ser Lys Asn
         35                  40                  45

Glu Ala Lys Lys Arg Met Lys Ala Leu Thr Gly Asp Ser Lys Lys Asp
 50                  55                  60

Ser Asp Leu Leu Trp Lys Val Trp Phe Ser Tyr Arg Glu Met Asn Tyr
 65                  70                  75                  80

Arg His Ser Trp Leu Thr Pro Phe Phe Ile Leu Val Cys Val Tyr Ser
                 85                  90                  95

Ala Tyr Phe Leu Ser Gly Asn Arg Thr Glu Ser Asn Pro Leu His Met
                100                 105                 110

Phe Val Ala Ile Ser Tyr Gln Val Asp Gly Thr Asp Ser Tyr Ala Lys
                115                 120                 125

Gly Ile Lys Asp Leu Ser Phe Val Phe Tyr Met Ile Phe Phe Thr
130                 135                 140

Phe Leu Arg Glu Phe Leu Met Asp Val Val Ile Arg Pro Phe Thr Val
145                 150                 155                 160

Tyr Leu Asn Val Thr Ser Glu His Arg Gln Lys Arg Met Leu Glu Gln
                165                 170                 175

Met Tyr Ala Ile Phe Tyr Cys Gly Val Ser Gly Pro Phe Gly Leu Tyr
                180                 185                 190

Ile Met Tyr His Ser Asp Leu Trp Leu Phe Lys Thr Lys Pro Met Tyr
                195                 200                 205

Arg Thr Tyr Pro Val Ile Thr Asn Pro Phe Leu Phe Lys Ile Phe Tyr
                210                 215                 220

Leu Gly Gln Ala Ala Phe Trp Ala Gln Gln Ala Cys Val Leu Val Leu
225                 230                 235                 240

Gln Leu Glu Lys Pro Arg Lys Asp Tyr Lys Glu Leu Val Phe His His
                245                 250                 255

Ile Val Thr Leu Leu Leu Ile Trp Ser Ser Tyr Val Phe His Phe Thr
                260                 265                 270

Lys Met Gly Leu Ala Ile Tyr Ile Thr Met Asp Val Ser Asp Phe Phe
                275                 280                 285

Leu Ser Leu Ser Lys Thr Leu Asn Tyr Leu Asn Ser Val Phe Thr Pro
290                 295                 300

Phe Val Phe Gly Leu Phe Val Phe Phe Trp Ile Tyr Leu Arg His Val
305                 310                 315                 320

Val Asn Ile Arg Ile Leu Trp Ser Val Leu Thr Glu Phe Arg His Glu
                325                 330                 335

Gly Asn Tyr Val Leu Asn Phe Ala Thr Gln Gln Tyr Lys Cys Trp Ile
                340                 345                 350

Ser Leu Pro Ile Val Phe Val Leu Ile Ala Ala Leu Gln Leu Val Asn
                355                 360                 365

Leu Tyr Trp Leu Phe Leu Ile Leu Arg Ile Leu Tyr Arg Leu Ile Trp
370                 375                 380

Gln Gly Ile Gln Lys Asp Glu Arg Ser Asp Ser Asp Ser Asp Glu Ser
385                 390                 395                 400

Ala Glu Asn Glu Glu Ser Lys Glu Lys Cys Glu
                405                 410
```